United States Patent

Gordon

(10) Patent No.: US 8,852,204 B2
(45) Date of Patent: Oct. 7, 2014

(54) MEDICAL SNARE DEVICE

(75) Inventor: Charles Samuel Squire Gordon, St. Pete Beach, FL (US)

(73) Assignee: Merit Medical Systems, Inc., South Jordan, UT (US)

( * ) Notice: Subject to any disclaimer, the term of this patent is extended or adjusted under 35 U.S.C. 154(b) by 152 days.

(21) Appl. No.: 12/873,447

(22) Filed: Sep. 1, 2010

(65) Prior Publication Data

US 2012/0053596 A1 Mar. 1, 2012

(51) Int. Cl.
*A61B 17/24* (2006.01)
*A61B 17/221* (2006.01)
A61B 17/22 (2006.01)

(52) U.S. Cl.
CPC ..... *A61B 17/221* (2013.01); *A61B 2017/22045* (2013.01); *A61B 2017/2212* (2013.01)
USPC .......................................................... 606/113

(58) Field of Classification Search
CPC ............. A61B 17/221; A61B 17/3205; A61B 17/32056; A61B 17/26; A61B 2017/2212; A61B 2017/22045
USPC ................. 606/110–114, 127–128, 159, 200; 600/585
See application file for complete search history.

(56) References Cited

U.S. PATENT DOCUMENTS

| | | | | |
|---|---|---|---|---|
| 4,215,703 A | * | 8/1980 | Willson | 600/585 |
| 4,846,186 A | * | 7/1989 | Box et al. | 600/434 |
| 5,171,233 A | * | 12/1992 | Amplatz et al. | 604/540 |
| 6,129,739 A | | 10/2000 | Khosravi | |
| 6,146,396 A | * | 11/2000 | Konya et al. | 606/159 |
| 6,517,550 B1 | * | 2/2003 | Konya et al. | 606/113 |
| 6,966,914 B2 | * | 11/2005 | Abe | 606/113 |
| 7,399,307 B2 | * | 7/2008 | Evans et al. | 606/194 |
| 7,655,013 B2 | | 2/2010 | Bieneman | |
| 2001/0000348 A1 | * | 4/2001 | Chu et al. | 606/113 |
| 2002/0188262 A1 | * | 12/2002 | Abe | 604/326 |
| 2003/0018354 A1 | * | 1/2003 | Roth et al. | 606/200 |
| 2004/0039304 A1 | * | 2/2004 | Connors et al. | 600/585 |
| 2004/0153119 A1 | * | 8/2004 | Kusleika et al. | 606/200 |
| 2004/0199201 A1 | | 10/2004 | Kellett et al. | |
| 2004/0225299 A1 | | 11/2004 | Carrison et al. | |
| 2005/0054953 A1 | * | 3/2005 | Ryan et al. | 600/585 |
| 2005/0085826 A1 | | 4/2005 | Nair et al. | |
| 2005/0171566 A1 | * | 8/2005 | Kanamaru | 606/159 |
| 2007/0043307 A1 | * | 2/2007 | Raulerson et al. | 600/585 |
| 2007/0135834 A1 | | 6/2007 | Clubb et al. | |

(Continued)

FOREIGN PATENT DOCUMENTS

WO WO2012/031149 3/2012

OTHER PUBLICATIONS http://dictionary.reference.com/browse/integral, retrieved Oct. 6, 2011.*
http://dictionary.reference.com/browse/sheath?s=t, retrieved Jun. 1, 2012.*

(Continued)

*Primary Examiner* — David Eastwood
(74) *Attorney, Agent, or Firm* — Stoel Rives LLP

(57) ABSTRACT

An apparatus having a longitudinal shaft. A guide feature is associated with the longitudinal shaft. The guide feature is disposed adjacent to a distal end of the longitudinal shaft. At least one ensnarement feature is associated with the longitudinal shaft. The at least one ensnarement feature is disposed at least partially proximally relative to the guide feature.

12 Claims, 20 Drawing Sheets

(56) References Cited

U.S. PATENT DOCUMENTS

| | | |
|---|---|---|
| 2008/0009883 A1* | 1/2008 | Bieneman .................... 606/113 |
| 2008/0294175 A1* | 11/2008 | Bardsley et al. ............. 606/113 |
| 2009/0054907 A1* | 2/2009 | Lowe et al. ................... 606/127 |
| 2010/0036312 A1* | 2/2010 | Krolik et al. .................... 604/22 |

OTHER PUBLICATIONS

International Search Report and Written Opinion, mailed Dec. 19, 2011, received in counterpart International Patent Application No. PCT/US2011/050245, 6 pgs.

\* cited by examiner

MEDICAL SNARE DEVICE

TECHNICAL FIELD

The present disclosure generally relates to medical snare devices, and more particularly relates to medical snare devices providing improved steering and/or tracking.

BACKGROUND OF THE DISCLOSURE

Medical snares are typically employed to extract foreign and/or undesired material from vessels within the body. For example, medical snares may be used for extracting blood clots from within the cardiovascular system, as well as stones from within the urinary and biliary systems. Similarly, medical snares may be used for removing foreign objects from the body. For example, medical snares may be used to remove objects such as stents, filters and catheters that have been inadvertently placed, which have broken free, and/or that may have migrated from other locations from within the body.

In a typical procedure utilizing a medical snare, a vascular sheath is inserted into the patient, for example into the femoral artery, to provide access to the cardiovascular system of the patent. A catheter is inserted through the vascular sheath, and a guide wire is inserted through the catheter. The guide wire is advanced through the vascular system to the desired location, e.g., to the vicinity of the clot to be removed. Once the guide wire has been positioned in the desired location, the catheter is advanced over the guide wire, thereby delivering the catheter to the area of interest, such as the vicinity of the clot, in the foregoing example. Once the guide wire has been removed from the catheter, a snare may be introduced through the catheter to the desired location. The snare, which may include one or more loops is advanced at least partially out of the catheter to capture the clot. Once the clot has been captured by the snare, the snare and catheter may be retracted as a unit, and ultimately removed from the patient via the vascular sheath.

Unfortunately, it is not uncommon that, once the catheter has been delivered to the site of interest, the catheter may move from the ideal position during the removal of the guide wire and subsequent advancement of the snare through the catheter. Such movement typically results in a failed snaring attempt. When the snaring attempt is unsuccessful, the snare must be removed from the catheter. The guide wire must then be reinserted through the catheter, and the catheter must be repositioned. Once the catheter has been repositioned, the snare may again be inserted through the catheter, and another snaring attempt may be made. Attempts to reposition the catheter without first removing the snare and reinserting and repositioning the guide wire may often damage the vessel, either by the leading edge of the catheter or by the snare itself if the snare is used out in front of the catheter during the repositioning attempt.

The need to "start over," by removing the snare, reinserting the guide wire, repositioning the catheter, and then reinserting the snare, in order to make another snaring attempt following a failed capture is undesirable. Such repeated snaring attempts are frustrating to the medical professionals carrying out the procedure, are time consuming, and potentially harmful to the patient, necessitating unnecessary radiation exposure. This is especially true considering the seriousness of the circumstances that necessitate the snaring procedure in the first place, e.g., a blood clot restricting blood flow to critical anatomy or presenting a risk of dislodging and moving to a critical region.

SUMMARY OF THE DISCLOSURE

According to a first embodiment, an apparatus includes a longitudinal shaft. A guide feature is associated with the longitudinal shaft. The guide feature is disposed adjacent to a distal end of the longitudinal shaft. The apparatus further includes at least one ensnarement feature associated with the longitudinal shaft. The at least one ensnarement feature is disposed at least partially proximally relative to the guide feature.

One or more of the following features may be included. The longitudinal shaft may include a flexible member. The longitudinal shaft may include a metallic wire. The longitudinal shaft may include a plurality of carbon fiber strands. The longitudinal shaft may include a hydrophilic surface.

The guide feature may include a curved distal end of the longitudinal shaft. The guide feature may include an integral feature of the longitudinal shaft. The guide feature may be coupled to the longitudinal shaft via the at least one ensnarement feature.

The at least one ensnarement feature may include at least one loop. The at least one loop may be oriented at an angle relative to an axis of the longitudinal shaft. The at least one ensnarement feature may include a basket feature. The basket feature may include a porous membrane. The basket feature may include an opening structure. The basket feature may include a variable opening diameter.

The apparatus may further include a catheter including a longitudinal lumen configured to slidingly receive at least a portion of the longitudinal shaft. The apparatus may include at least one radiopaque marker.

According to another embodiment, an apparatus includes a catheter, and a snare configured to be least partially slidably disposed within the catheter. The snare includes a longitudinal shaft. A guide feature is disposed adjacent the longitudinal shaft. The guide feature provides a curved distal end of the longitudinal shaft. The apparatus also includes at least one loop disposed at least partially proximal relative to the guide feature.

The snare may include one or more filaments disposed within a hydrophilic sheath.

According to yet another embodiment, an apparatus includes a catheter, and a snare configured to be at least partially slidably disposed within the catheter. The snare includes a longitudinal shaft. A guide feature is disposed adjacent the longitudinal shaft. The guide feature provides a curved distal end of the longitudinal shaft. The apparatus also includes a basket feature disposed at least partially proximal relative to the guide feature.

The snare may include one or more filaments disposed within a hydrophilic sheath.

The details of one or more implementations are set forth in the accompanying drawings and the description below. Other features and advantages will become apparent from the description, the drawings, and the claims.

DETAILED DESCRIPTION OF THE DISCLOSURE

Figure 1:
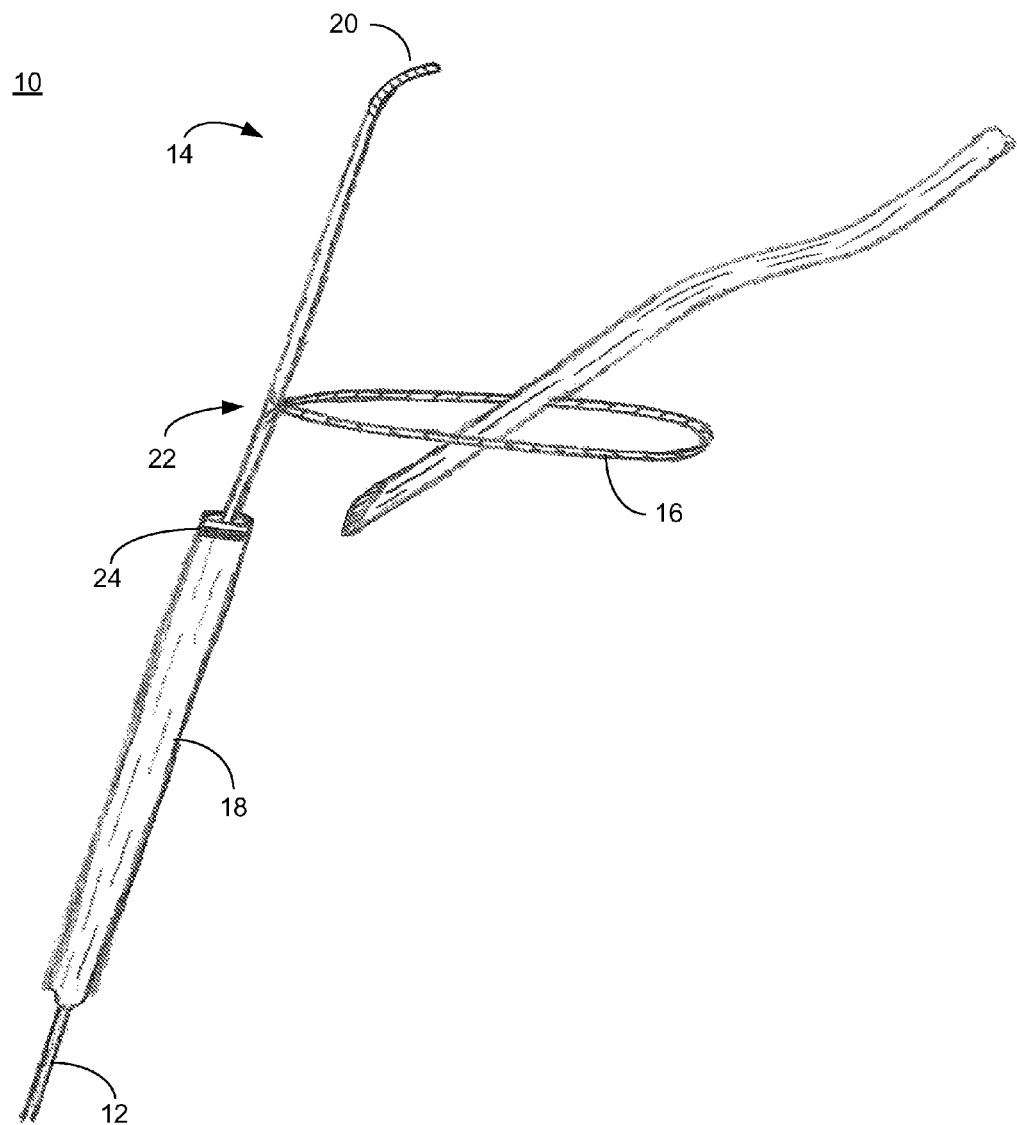
FIG. 1 depicts an embodiment of a snare assembly including a loop-type ensnarement feature.

Referring to FIG. 1, an embodiment of snare assembly 10 may generally include longitudinal shaft 12. Guide feature 14 may be associated with longitudinal shaft 12. As shown, guide feature 14 may be disposed adjacent to a distal end of longitudinal shaft 12. Snare assembly 10 may further include at least one ensnarement feature (e.g., loop 16 shown in the embodiment of FIG. 1). The ensnarement feature (e.g., loop 16) may be disposed at least partially proximally relative to guide feature 14. In some embodiments, snare assembly 10 may further include catheter 18, including a longitudinal lumen configured to slidingly receive at least a portion of longitudinal shaft 12, and/or at least a portion of one or more of the ensnarement feature and guide feature 14. Snare assembly 10 may be sized according to the anatomic structure of interest (e.g., to allow facile movement of snare assembly 10 through various anatomic lumens from a site of insertion of snare assembly 10 to the location of a body to be removed using snare assembly 10). In one embodiment, catheter 18 may include a 4 French or a 5 French catheter. However, it will be appreciated that various additional/alternative sizes may be utilized depending upon the anatomic structures that may be negotiated during the snare procedure.

Snare assembly 10 may be utilized for the capture and removal of various bodies from within a patient. For example, snare assembly 10 may be employed for the capture and removal of arterial emboli, arterial thrombi, venous emboli, venous thrombi, urinary stones, biliary stones, and foreign bodies from within various anatomical locations, including, but not limited to the cardiovascular system, the biliary system, and the urinary system. The foregoing examples of bodies that may be captured and removed using snare assembly 10, and the foregoing examples of anatomical locations in which snare assembly 10 may be utilized are provided for the purpose of example only, and should not be construed as a limitation of the present disclosure. Snare assembly 10 may be equally utilized for the capture and removal of various other bodies, and in various other anatomical locations.

Longitudinal shaft 12 may generally include a resiliently flexible (i.e., elastically deformable allowing at least some degree of elastic deformation and elastic recovery) member. For example, longitudinal shaft 12 may include a metallic wire. For example, longitudinal shaft 12 may include an elastic and/or shape memory metallic alloy wire. Examples of suitable elastic metallic wire may include, but is not limited to, titanium, titanium-nickel alloys (such as Nitinol). Longitudinal shaft 12 may include a single metallic wire. Further, longitudinal shaft 12 may include a plurality of metallic wires bound together to provide a single shaft. For example, a plurality of metallic wires may be bound together by an outer sheath, a coating, a binding agent (such as an adhesive), may be twisted together, or the like. In this regard, the plurality of metallic wires may be oriented generally parallel to one another and generally parallel to the axis of longitudinal shaft 12. Additionally/alternatively one or more of the metallic wires may be oriented at an angle to the axis of longitudinal shaft, e.g., being generally helically wound relative to the axis of longitudinal shaft 12 and/or relative to an axis of one or more other metallic wires.

Further, longitudinal shaft 12 may additionally/alternatively include one, or a plurality of, carbon fiber strands. In a similar manner as described above with respect to the implementation of metallic wires, a plurality of carbon fiber strands may be bound together to provide a single shaft. The plurality of carbon fiber strands may be bound together by an outer sheath, a coating, a binding agent, by being twisted, or the like. Further, and also as described above with respect to the implementation of metallic wires, the plurality of carbon fiber strands may be generally oriented parallel to one another and generally parallel to the axis of longitudinal shaft 12. Additionally/alternatively one or more of the carbon fiber strands may be oriented at an angle relative to the axis of longitudinal shaft 12 and/or relative to an axis of one or more of the other carbon fiber strands.

While metallic wire and carbon fiber strands have been described above, this is for the purpose of illustration, and should not be construed as a limitation of the present disclosure. Various additional/alternative materials may equally be utilized (e.g., nano-materials such as carbon nanotubes or the like, polymeric filaments or strands, etc.). Additionally, longitudinal shaft 12 may include one or more different materials. For example, longitudinal shaft 12 may include one or more metallic wires in combination with one or more carbon fiber strands. The one or more metallic wires and the one or more carbon fiber strands may be bound together, as described above.

Longitudinal shaft 12 may include a hydrophilic surface. The hydrophilic surface may, for example, reduce friction of longitudinal shaft 12, which may facilitate movement of longitudinal shaft. For example, the hydrophilic surface may reduce friction of longitudinal shaft 12 moving relative to catheter 18, and/or relative to any anatomic features encountered by longitudinal shaft 12. In one embodiment, longitudinal shaft may include a shrink wrap material disposed over the one or more strands making up longitudinal shaft 12. The shrink wrap material may include a hydrophilic outer surface. Accordingly, the shrink wrap material may not only provide a hydrophilic surface of longitudinal shaft 12, the shrink wrap material may also (alone or in combination with one or more of the above describe techniques) bond together the strands making up longitudinal shaft 12. In further embodiments, the hydrophilic surface may be provided by a surface treatment of the one or more wires, strands, or the like, making up longitudinal shaft 12, and/or may include an applied coating.

Guide feature 14 may include curved distal end 20. As described above, guide feature 14 may be disposed adjacent a distal end of longitudinal shaft 12. Accordingly, guide feature 14 may provide a curved distal end of longitudinal shaft 12. Curved distal end 20 may improve the steerability of longitudinal shaft 12. For example, longitudinal shaft 12 may be at least partially torsionally rigid. That is, while longitudinal shaft 12 may include some degree of torsional compliance, a rotation of a proximal end of longitudinal shaft 12 may effect a rotation of curved distal end 20. Accordingly, as longitudinal shaft 12 is advanced through an anatomical lumen (e.g., a vein, artery, or the like) a proximal end of longitudinal shaft 12 may be rotated causing curved distal end 20 to rotated. Accordingly, for example, upon reaching a branch in the anatomical lumen, in which it is desired to advance longitudinal shaft 12 through the branch, longitudinal shaft 12 may be rotated (e.g., by rotation of a proximal end of longitudinal shaft 12 effecting a corresponding, although not necessarily proportional, rotation of curved distal end) to orient curved distal end 20 along the desired path of travel of longitudinal shaft 12 (e.g., down the branch of the anatomical lumen, in the foregoing example). With the desired orientation of curved distal end 20 achieve, longitudinal shaft 12 may be further advanced. Curved distal end 20 may allow longitudinal shaft 12 to enter the branch of the anatomical lumen. For example, curved distal end 20 may at least partially enter the branch of the anatomical lumen as a result of the desired orientation being achieved. Additionally/alternatively, the arcuate aspect of curved distal end 20 may contact the junction of the branch (and/or a wall of the branch adjacent to the junction) as longitudinal shaft 12 is advanced. Contact by the arcuate aspect of curved distal end 20 (e.g., as opposed to a blunt or pointed aspect) may allow guide feature 14 and/or longitudinal shaft 12 to elastically deflect to enter the branch while cause no, or an acceptable degree, of damage to the tissue of the anatomical lumen. The above-described steering procedure may be employed throughout the advancement of longitudinal shaft 12 to the desired site (e.g., the body to be removed from the patient).

Consistent with the foregoing description, guide feature 14 may allow the number of steps necessary for a snaring procedure to be reduced. For example, rather than first introducing a guide wire, advancing a catheter over the guide wire, then subsequently removing the guide wire and then inserting a snare, guide feature 14 may allow snare assembly 10 to be directly inserted and advanced to a desired location in a single step (e.g., not necessitating the use of a separate guide wire, advancement of the catheter over the guide wire, and subsequent insertion of the snare).

Guide feature 14 may include an integral feature of longitudinal shaft 12. For example the one or more metallic wires, carbon fiber strands, etc., may extend distally of the main body of longitudinal shaft 12, and may provide guide feature 14, including curved distal end 20. Curved distal end 20 may be formed, e.g., by bending the end of longitudinal shaft 12, by utilizing differential lengths of the various strands making up longitudinal shaft 12, or the like.

Figure 4:
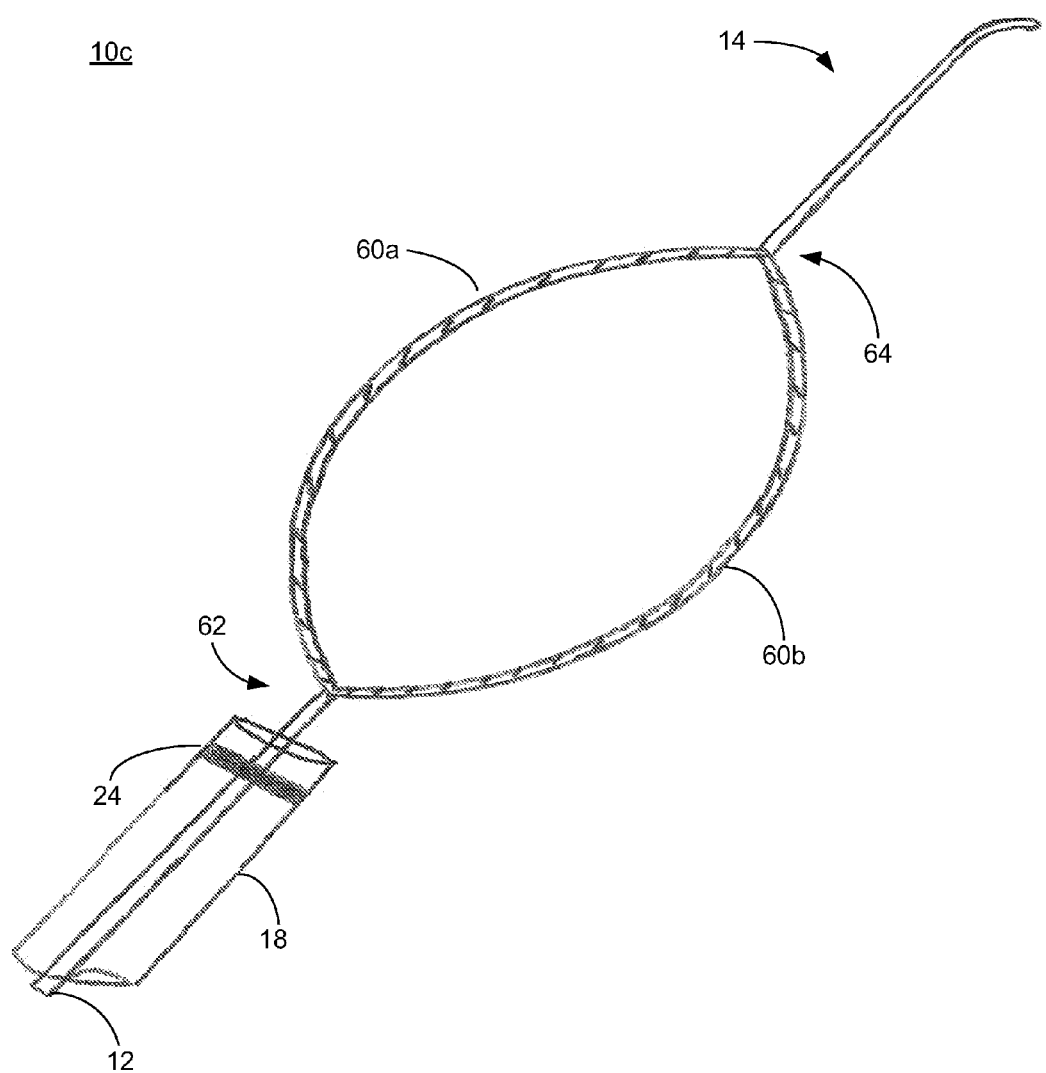
FIG. 4 depicts another embodiment of a snare assembly including a loop-type ensnarement feature.
Figure 5:
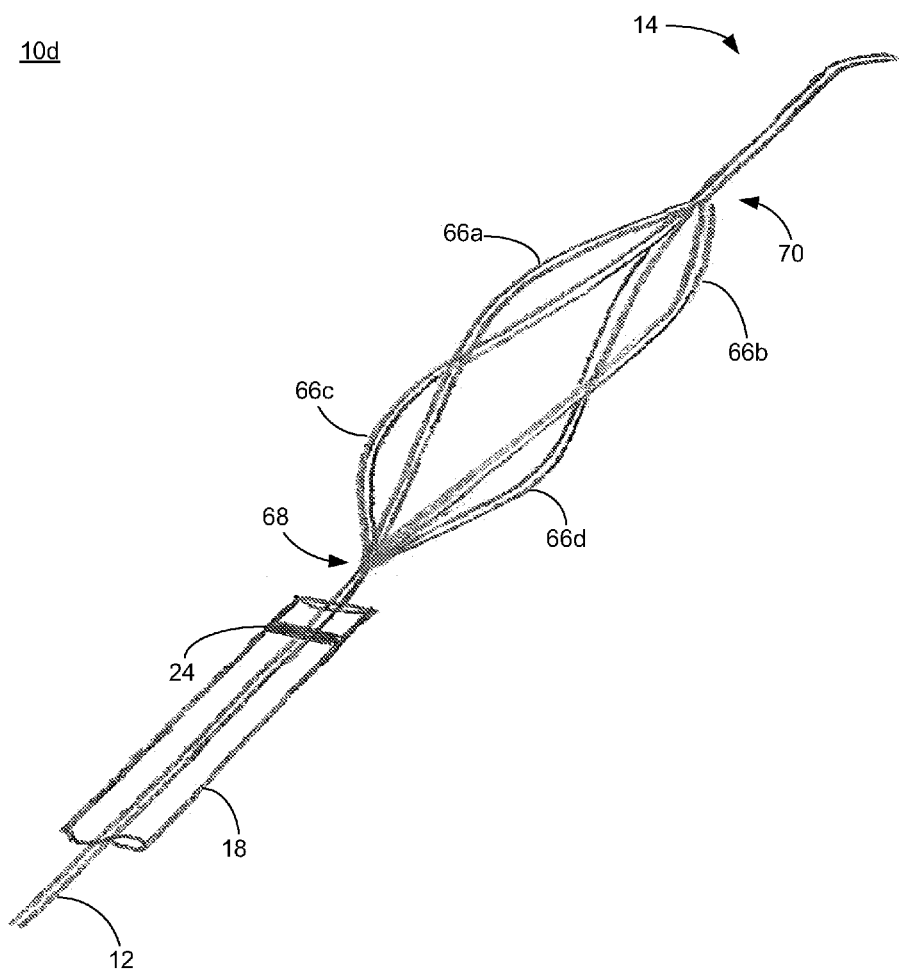
FIG. 5 depicts another embodiment of a snare assembly including a loop-type ensnarement feature.
Figure 6:
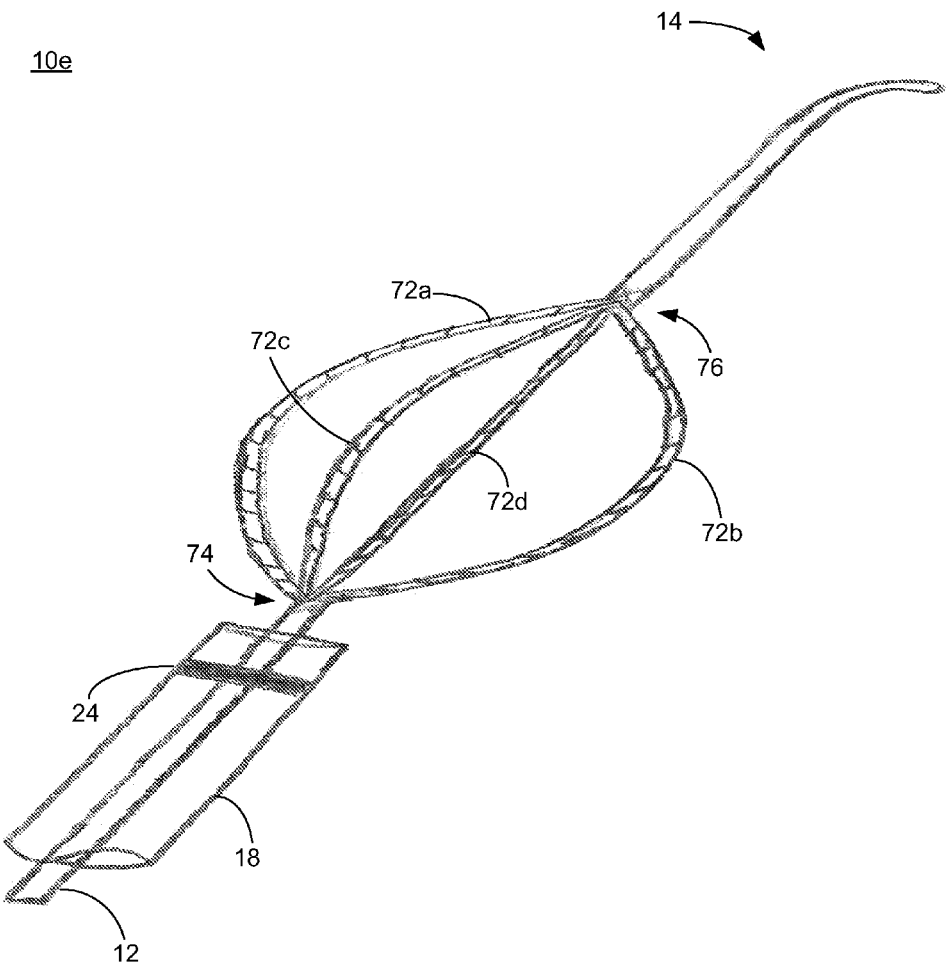
FIG. 6 depicts yet another embodiment of a snare assembly including a loop-type ensnarement feature.

In further embodiments, guide feature 14 may be a separate component/structure that may be coupled to longitudinal shaft 12. For example, guide feature 14 may be coupled to longitudinal shaft 12 via the at least one ensnarement feature (e.g., as generally shown in FIGS. 4 through 6). For example, and as will be discussed below, the one or more strands making up longitudinal shaft 12 may be at least partially separated from one another to form the at least one ensnarement feature. At least a portion of the at least partially separated strands may be at least partially rejoined with one another to form guide feature 14. In further embodiments, guide feature 14 may be coupled to the at least one ensnarement feature (e.g., which may itself be coupled to/integral with longitudinal shaft 12). For example, guide feature 14 may be coupled to the at least one ensnarement feature utilizing a crimp connection, bonding (e.g., welding, adhesive bonding, etc.), a shrink wrap material, or the like.

Similar to longitudinal shaft 12, guide feature 14 may include a resiliently flexible material, such as one or more elastically deflectable metallic wires, one or more carbon fiber strands, or the like. Also similar to longitudinal shaft 12, guide feature 14 may include hydrophilic coating. For example, guide feature 14 may include a sheath or coating including a shrink wrap material. The shrink wrap material may include a hydrophilic surface. In some embodiments, guide feature 14 may be configured to relatively more flexible than longitudinal shaft 12. For example, the flexibility of guide feature 14 may allow guide feature 14 to at least partially deflect when urged against an inner wall of an anatomic lumen. Accordingly, guide feature 14 may, e.g., in response to at least partially deflecting when urged against an inner wall of an anatomic lumen, track along the path of the anatomic lumen (and/or track along a branch of the anatomic lumen) without puncturing or penetrating a wall of the anatomic lumen (or branch thereof).

As shown with reference to FIG. 1, the at least one ensnarement feature may include a loop (e.g., loop 16). The ensnarement feature (e.g., loop 16) may include a resiliently flexible material. For example, the ensnarement feature may include one or more metallic wires, carbon fiber strands, or the like, as described above with respect to longitudinal shaft 12 and guide feature 14. Additionally, and as described above with reference to longitudinal shaft 12 and guide feature 14, the ensnarement feature may include a hydrophilic surface, e.g., in the form of a shrink wrap material having a hydrophilic surface, in the form of a surface treatment of the material making up the ensnarement feature itself, or in the form of an applied coating.

Loop 16 may be integral with longitudinal shaft 12 and/or guide feature 14. For example, at least a portion of the one or more metallic wires or carbon fiber strands may be shaped to form loop 16, and may further continue distally to provide guide feature 14. Additionally/alternatively, loop 16 may include a separate structure coupled to longitudinal shaft 12 and/or to guide feature 14. In such an embodiment, loop 16 may be coupled to longitudinal shaft 12 and/or to guide feature 14 using a crimp connection, by bonding (e.g., welding or adhesive bonding), via a shrink wrap material (e.g., a shrink wrap sheath), or the like. In any of the foregoing variants, at least a portion of guide feature 14 (e.g., curved distal end 20) may extend distally beyond the ensnarement feature.

The at least one loop (e.g., loop 16 in FIG. 1) may be oriented at an angle relative to an axis of longitudinal shaft 12. That is, a plane in which loop 16 lies (e.g., which may include an average plane, in the circumstance in which loop 16 may be non-planar) may be oriented at an angle relative to the axis of longitudinal shaft 12. According to an embodiment, loop 16 may be oriented at an angle of between about +/−45 degrees and about 90 degrees relative to the axis of longitudinal shaft 12. However, the foregoing angular orientation is provided for the purpose of illustration only, as the angular orientation between loop 16 and an axis of longitudinal shaft 12 may vary according to design criteria and user need.

As shown in FIGS. 1 through 6 snare assembly 10 may include loop-type ensnarement features having a variety of different configurations. Referring to FIG. 1, snare assembly 10 may include a single loop (i.e., loop 16) generally having a single attachment point (e.g., attachment point 22) to longitudinal shaft 12/guide feature 14. As also shown in FIG. 1, loop 16 may be oriented at an angle relative to an axis of longitudinal shaft 12.

Figure 2:
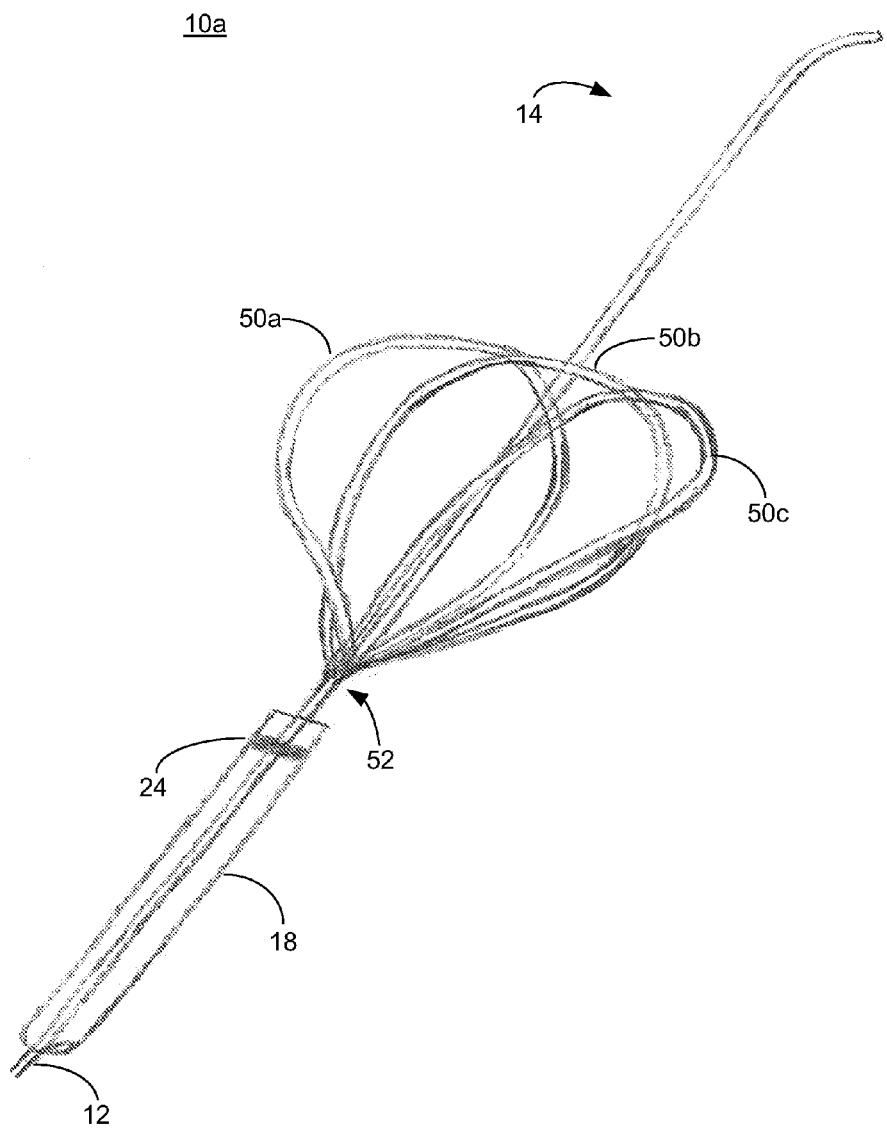
FIG. 2 depicts another embodiment of a snare assembly including a loop-type ensnarement feature.

Referring to FIG. 2, snare assembly 10a may include an ensnarement feature configured as a plurality of loops, namely loops 50a, 50b, 50c. Similar to loop 16, the loops 50a, 50b, 50c may generally have a single attachment point (e.g., attachment point 52) relative to longitudinal shaft 12/guide feature 14. Loops 50a, 50b, 50c may generally be oriented at an acute angle relative to the distal end of longitudinal shaft 12/guide feature 14, however other angular orientations may be suitably utilized. Additionally, loops 50a, 50b, 50c may be disposed at differing radial angular orientations relative to longitudinal shaft 12/guide feature 14.

Figure 3:
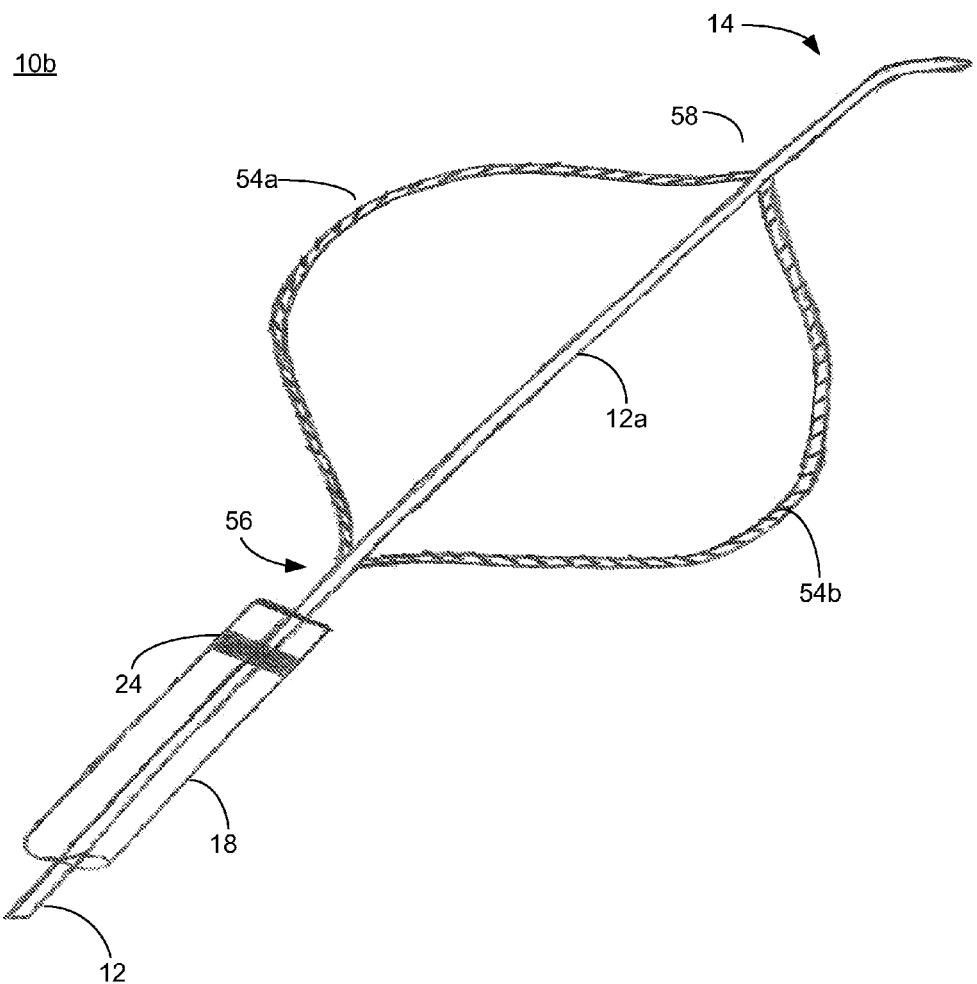
FIG. 3 depicts another embodiment of a snare assembly including a loop-type ensnarement feature.

With reference to FIG. 3, snare assembly 10b may include two loop-type ensnarement features, namely loop 54a and loop 54b. Loops 54a, 54b may be coupled to/extend from longitudinal shaft 12, guide feature 14 via proximal attachment point 56 and distal attachment point 58. While not a requirement of the present disclosure, loops 54a, 54b may be generally coaxial with longitudinal shaft 12 (i.e., loops 54a, 54b may generally lie in a plane that is parallel with the axis of longitudinal shaft 12). Additionally, loops 54a, 54b may generally extend laterally from longitudinal shaft 12/guide feature 14, which may extend generally continuously, including intermediate portion 12a disposed between proximal attachment point 56 and distal attachment point 58.

Similar to the previous embodiment, FIG. 4 depicts snare assembly 10c including loop portions 60a, 60b, which may generally provide a single loop-type ensnarement feature. Loop portions 60a, 60b may be proximally coupled to longitudinal shaft 12 at proximal attachment point 62. Further loop portions 60a, 60b may be distally coupled to guide feature 14 at distal attachment point 64. As shown, longitudinal shaft 12/guide feature 14 may be discontinuous in the region between proximal attachment point 62 and distal attachment point 64.

Referring to FIG. 5, snare assembly 10d may include loop portions 66a, 66b, 66c, 66d that may generally provide to loop-type ensnarement features. Loop portions 66a, 66b, 66c, 66d may be proximally coupled to longitudinal shaft 12 at proximal attachment point 68. Further loop portions 66a, 66b, 66c, 66d may be distally coupled to guide feature 14 at distal attachment point 70. As shown, longitudinal shaft 12/guide feature 14 may be discontinuous in the region between proximal attachment point 68 and distal attachment point 70. As also shown, loop portions 66a, 66b may generally form a first loop, and loop portions 66c, 66d may generally form a second loop. The first and second loops may be at least partially intertwined, e.g., by being at least partially rotated relative to one another about the axis of longitudinal shaft 12/guide feature 14. While not shown, the first and second loops, or a portion thereof (e.g., one or more of loop portions 66a, 66b, 66c, 66d) may be axially offset. For example, one or more of loop portions 66a, 66b, 66c, 66d may include a proximal and/or distal attachment point that is different from at least another of loop portions 66a, 66b, 66c, 66d.

Referring to FIG. 6, snare assembly 10e may include loop portions 72a, 72b, 72c, 72d that may generally provide to loop-type ensnarement features. Loop portions 72a, 72b, 72c, 72d may be proximally coupled to longitudinal shaft 12 at proximal attachment point 74. Further loop portions 72a, 72b, 72c, 72d may be distally coupled to guide feature 14 at distal attachment point 70. Similar to snare assembly 10c and 10d, shown in FIGS. 4 and 5 respectively, longitudinal shaft 12/guide feature 14 may be discontinuous in the region between proximal attachment point 74 and distal attachment point 76. As also shown, loop portions 72a, 72b, 72c, 72d may be at least partially rotated relative to one another about the axis of longitudinal shaft 12/guide feature 14. Further, and as discussed with respect to snare assembly 10d, one or more of loop portions 72a, 72b, 72c, 72d may be axially offset. For example, one or more of loop portions 72a 72b, 72c, 72d may include a proximal and/or distal attachment point that is different from at least another of loop portions 72a, 72b, 72c, 72d.

In any of the foregoing embodiments including loop-type ensnarement features, the loops may be utilized to explicitly snare a body to be removed from a patient (as will be described in detail below), by at least partially encircling the body and allowing extraction thereof. Further, in some embodiments, e.g., which may utilized a plurality of loop-type ensnarement features (e.g., as shown in FIGS. 2, 5, and 6), in addition to snaring a body by at least partially encircling the body, the plurality of loop-type ensnarement features may, when deployed, create a basket-type effect within the anatomic lumen. The basket-type effect may allow the body to be removed to become entangled in one or more of the plurality of loops. The entangled body may be subsequently extracted using the snare assembly.

Figure 7:
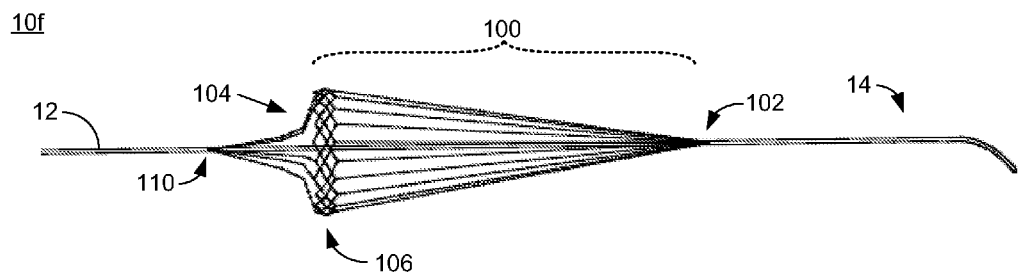
FIG. 7 depicts an embodiment of a snare assembly including a basket-type ensnarement feature.
Figure 8:
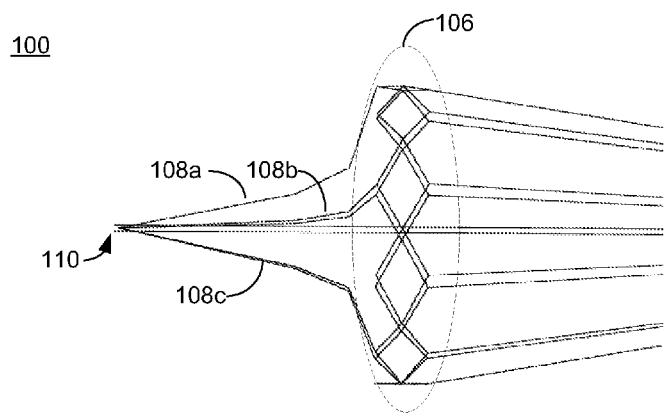
FIG. 8 is a detailed view of an opening structure of the basket-type ensnarement feature of FIG. 7.
Figure 9:
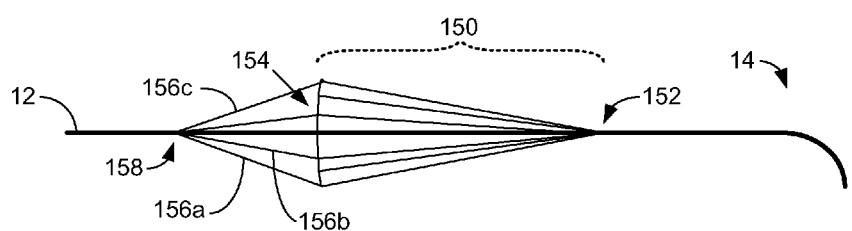
FIG. 9 depicts another embodiment of a snare assembly including a basket-type ensnarement feature.

With reference also to FIGS. 7 through 9, the at least one ensnarement feature may include a basket feature. Referring to FIG. 7, generally, snare assembly 10f may include basket feature 100. Basket feature 100 may include a membrane having a distal end coupled to longitudinal shaft 12/guide feature 14 at attachment point 102. Basket feature 100 may be coupled to longitudinal shaft 12/guide feature 14, for example, by a crimp connection, bonding (e.g., welding, adhesive bonding, etc.), a shrink wrap material, or other suitable means. At least a portion of guide feature 14 may extend distally beyond attachment point 102. Basket feature 100 may have a generally conical, semi-spherical, pyramidal, etc., geometry with proximal opening 104, generally. Proximal opening 104 may be configured to allow a body to be captured to enter basket feature 100, while being prevented from exiting distally by the membrane.

The membrane may include, for example, a polymeric film such as, but not limited to, a polyethylene film, a polypropylene film, a polyester film, or other suitable material. According to various embodiments, the membrane may include a porous membrane or a non-porous membrane. In a porous configuration, the membrane may include one or more perforations and/or cutouts. The porous membrane may, for example, allow a body to be extracted from an anatomic lumen while still permitting fluid to pass through the porous membrane. However, in other implementations the use of a non-porous membrane may be desirable, e.g., to prevent small pieces of a body being extracted from an anatomic lumen from breaking free and migrating to other anatomic locations/remaining at the site of extraction. The membrane may be reinforced by one or more reinforcement features, for example, by a plurality of filaments, a mesh structure, etc. The reinforcement features may be bonded to a single layer of membrane and/or may be sandwiched between two or more layers of membrane (e.g., which may be at least partially bonded together). The reinforcement features may include, but are not limited to, for example, ultrahigh molecular weight polyethylene (e.g., Spectra® fiber), carbon fiber, metallic wire, synthetic fiber (e.g., polyester fiber, nylon fiber, Kevlar® fiber, etc.), or other suitable material.

Basket feature 100 may include an opening structure (e.g., opening structure 106), for example, which may facilitate expansion of proximal opening 100 to an open configuration upon deployment of basket feature from catheter 18. With additional reference to FIG. 8, an embodiment of opening structure 106 may include a ring of quadrilaterals or rhombuses, for example. The ring of quadrilaterals or rhombuses may be made of a resilient material, such as an elastic or shape memory material (e.g., Nitinol, or the like) that may be collapsed for insertion into catheter 18, and which may expand upon being deployed from catheter 18 to effectuate opening of proximal opening 104. At least a portion of opening structure 106 may be coupled to and/or disposed at least partially within the membrane such that elastic recovery of opening structure 106 upon deployment from catheter 18 may open the proximal opening 104 of the membrane.

While not shown, various additional/alternative opening structures may be utilized. For example one or more loop-type ensnarement features may be coupled to, or disposed at least partially within, basket feature 100. Upon deployment from catheter 18 the one or more loop-type ensnarement features may resiliently expand, thereby also causing basket feature 100 to open. Various additional/alternative opening structures will be readily appreciated.

The basket feature may include a variable opening diameter. For example, opening structure 106 may resiliently bias proximal opening 104 towards a maximally open configuration (e.g., which may be based upon, at least in part, the cross-sectional area of the basket feature in the region of proximal opening 104. As such, basket feature 100 may expand to generally conform to the inner walls of the anatomic lumen (or the maximal open configuration, whichever is smaller).

Additionally, the opening of proximal opening 104 of basket feature 100 may be at least partially controllable by the user of snare assembly 10f. For example, opening structure 106 may be coupled to longitudinal shaft 12 by a plurality of arms (e.g., arms 108a, 108b, 108c visible in FIG. 8). While three arms (namely 108a, 108b, 108c) are shown in FIG. 8, this should not be construed as a limitation of the present disclosure as the number of arms may vary depending upon design criteria and user need. Arms 108a, 108b, 108c may be attached to proximal attachment point 110 (relative to proximal opening 104 of basket feature 100) on longitudinal shaft 12. In an embodiment, arms 108a, 108b, 108c may include resiliently flexible members, such as metallic wires (such as Nitinol shape memory alloy, etc), carbon fiber strands, or the like. Arms 108a, 108b, 108c may be resiliently biased outwardly away from longitudinal shaft 12, thereby also biasing proximal opening 104 towards an open position. As arms 108a, 108b, 108c may extend from proximal attachment point 110 on longitudinal shaft 12 to opening structure 106, interaction between arms 108a, 108b, 108c and an inner distal opening of catheter 108 may effectively shorten arms 108a, 108b, 108c when proximal attachment point 110 is at least partially retracted within catheter 18. The effective shortening of arms 108a, 108b, 108c may restrict the open dimension of proximal opening 104. As such, the size of proximal opening 104 may be at least partially controlled by controlling the relative position of proximal attachment point 110 within catheter 18. According to a further embodiment, arms 108a, 108b, 108c may have a generally concave geometry, with the concavity facing generally outwardly from longitudinal shaft 12. In one embodiment, the concave geometry of arms 108a, 108b, 108c may include a plurality of generally linear segments. The variable opening of basket feature 100 may allow a single snare assembly to be utilized in a variety of anatomic lumens and/or locations within anatomic lumens that have greatly varying sizes.

According to various embodiments one or more of the membrane, opening structure 106, and arms 108a, 108b, 108c may include laser cut components (e.g., in which various components may be laser cut from a single piece of alloy or membrane) thereby eliminating and/or minimizing welded parts or joints, e.g., which may be more susceptible to failure than single component laser cut parts.

Referring to FIG. 9, another embodiment of a snare assembly including a basket ensnarement feature is shown. Snare assembly 10g may include basket feature 150. Similar to basket feature 100, basket feature 150 may generally include a membrane (e.g., either porous or non-porous, as described above) having a distal end coupled to longitudinal shaft 12/guide feature 14 at attachment point 152. Basket feature 150 may be coupled to longitudinal shaft 12/guide feature 14, for example, by a crimp connection, bonding (e.g., welding, adhesive bonding, etc.), a shrink wrap material, or other suitable means. At least a portion of guide feature 14 may extend distally beyond attachment point 102. Basket feature 150 may have a generally conical, semi-spherical, pyramidal, etc., geometry with proximal opening 154, generally. Proximal opening 154 may be configured to allow a body to be captured to enter basket feature 150, while being prevented from exiting distally by the membrane. The membrane may be reinforced by one or more reinforcement features, for example, by a plurality of filaments, a mesh structure, etc. The reinforcement features may be bonded to a single layer of membrane and/or may be sandwiched between two or more layers of membrane (e.g., which may be at least partially bonded together). The reinforcement features may include, but are not limited to, for example, ultrahigh molecular weight polyethylene (e.g., Spectra® fiber), carbon fiber, metallic wire, synthetic fiber (e.g., polyester fiber, nylon fiber, Kevlar® fiber, etc.), or other suitable material.

Figure 10:
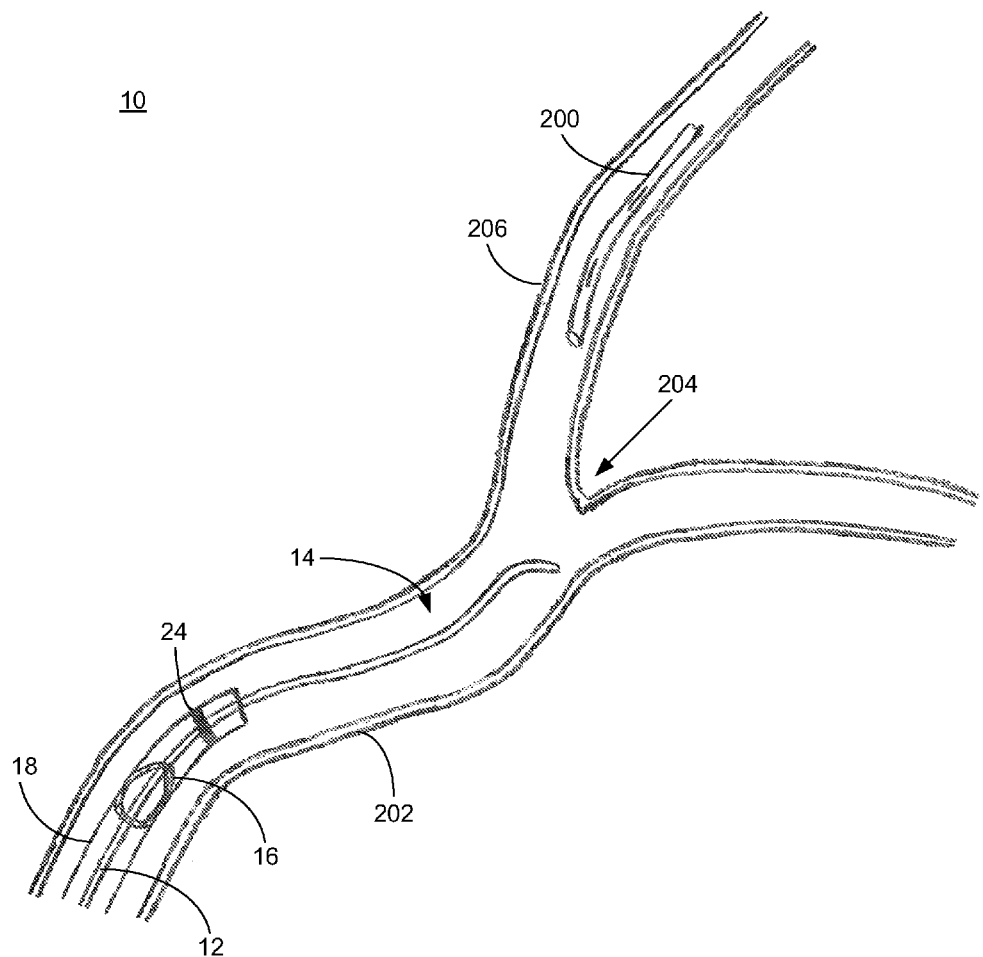
FIGS. 10-12 depicts the snare assembly of FIG. 1 utilized for extracting a catheter fragment from a vascular lumen.

A proximal portion of the membrane of basket feature 150 may be coupled to longitudinal shaft 12 by a plurality of arms (e.g., arms 156a, 156b, 156c visible in FIG. 10). While three arms (namely 156a, 156b, 156c) are shown in FIG. 9, this should not be construed as a limitation of the present disclosure as the number of arms may vary depending upon design criteria and user need. Arms 156a, 156b, 156c may be attached to proximal attachment point 158 (relative to proximal opening 104 of basket feature 100) on longitudinal shaft 12. In an embodiment, arms 156a, 156b, 156c may include resiliently flexible members, such as metallic wires (such as Nitinol shape memory alloy, etc), carbon fiber strands, or the like.

By contrast to snare assembly 10f, shown in FIGS. 7 and 8, snare assembly 10g may be provided without an opening structure. Accordingly, basket feature 150 may include only the membrane and reinforcing structure bonded thereto (or sandwiched between two or more layers of membrane). As such, basket feature may be strong and exhibit a thin profile. Basket feature 150 may open, once at least proximal opening 154 is deployed from catheter 18, as a result of relative fluid flow within the anatomic lumen. That is, fluid (such as blood, etc.) flowing in the anatomic lumen in a direction generally distally relative to snare assembly 10g may urge basket feature 150 towards the open position. Similar apparent fluid flow may be induced in generally static (e.g., non-flowing) fluid by moving basket feature 150 in a proximal direction. Drag induced by static fluid within the anatomic lumen when basket feature 150 is moved proximally may urge basket feature toward an open position.

As with basket feature 100, basket feature 150 may open to generally conform to the inner walls of the anatomic lumen. Additionally, proximal opening 154 may be at least partially controlled based upon the interaction between arms 156a, 156b, 156c and an inner proximal opening of catheter 18, as described above with respect to snare assembly 10f.

The snare assembly (e.g., snare assembly 10, 10a, 10b, 10c, 10d, 10e, 10f, 10g) may include at least one radiopaque marker. The at least one radiopaque marker may facilitate positioning of catheter 18 and/or the ensnarement feature within the anatomic structure (e.g., relative to a body to be extracted). Similarly, the at least one radiopaque marker may facilitate guiding the snare assembly to the desired anatomic location. The radiopaque marker may include, but is not limited to, a noble metal such as gold or platinum, as well as materials such as barium powder, which may be incorporated into catheter 18 and/or disposed between layers of membrane. One or more radiopaque markers may be associated with catheter 18, longitudinal shaft 12, guide feature 14, and the ensnarement feature. For example, as shown in FIGS. 1 through 6, catheter 18 may include radiopaque marker 24, e.g., which may include a band of platinum or gold disposed adjacent the distal end of catheter 18. Radiopaque marker 24 may allow the location of catheter to be monitored using conventional imaging, such as fluoroscopy. Similarly, one or more of guide feature 14 and the ensnarement feature may include one or more radiopaque markers. For example, as shown in FIG. 1, curved distal end 20 of guide feature 14 may include a radiopaque marker (indicated by hash lines in FIG. 1). Similarly, as indicated by hash lines in FIG. 1, loop 16 may include one or more radiopaque markers. While not particularly called out, the various other embodiments may include similar radiopaque markers, as will be readily understood. Accordingly, the radiopaque markers may allow a user to monitor the position of various aspects of the snare assembly, thereby facilitating the movement of the snare assembly through the anatomy of a patient, and the placement of the snare assembly and capture of a body to be removed from the patient.

While attachment points of ensnarement features have been identified in the foregoing description, it will be appreciated that such identification has been provided for the purposed of identifying relative structural attributes. As described herein-above, any of the various ensnarement features may be integrally formed with longitudinal shaft 12 and/or guide feature 14, e.g., with portions of the one or more metallic wires, carbon fiber strands, or the like, of longitudinal shaft 12 and/or guide feature 14 forming the various ensnarement features. Additionally/alternatively, the various ensnarement features may include a separate component that may be coupled to one or more of longitudinal shaft 12 and guide feature 14. Accordingly, while the present disclosure is intended to include ensnarement features including separate components coupled to one or more of longitudinal shaft 12 and guide feature 14, the present disclosure is similarly intended to include ensnarement features in which at least a portion of the ensnarement feature is integral with one or more of longitudinal shaft 12 and guide feature 14.

Figure 11:
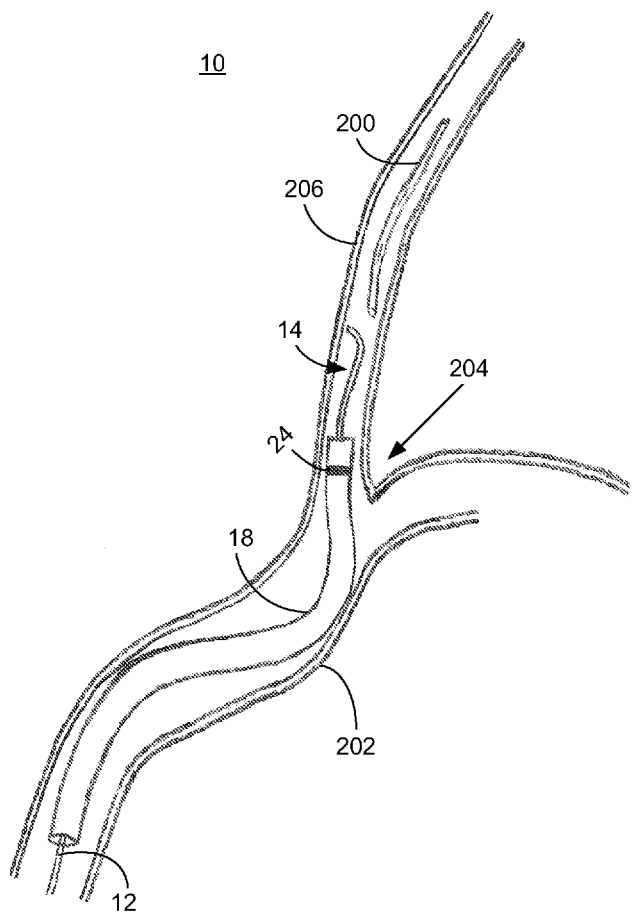
Figure 12:
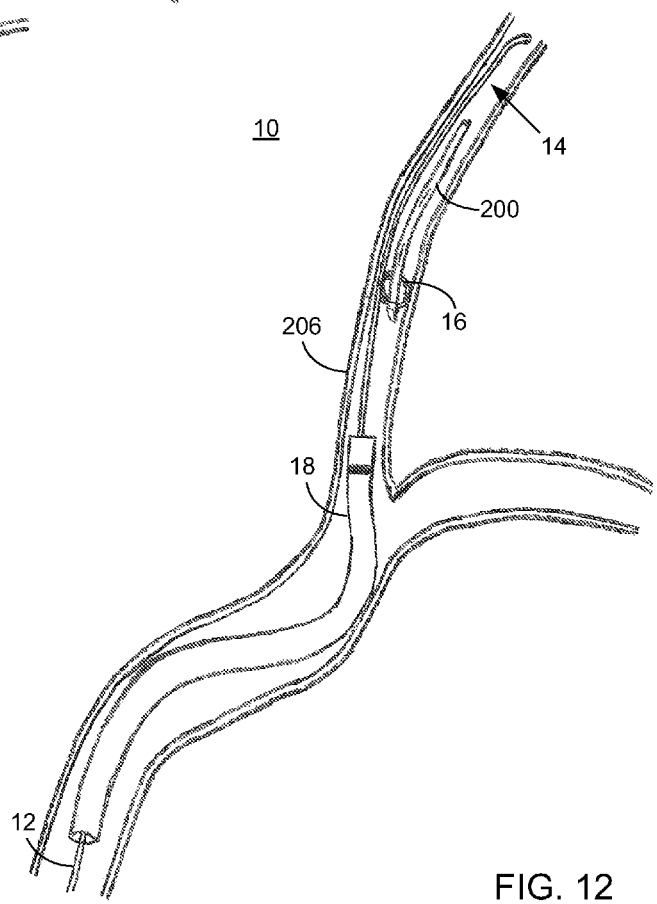

Referring to FIGS. 10 through 12, snare assembly 10 may be employed to remove a body (e.g., a portion of sheared off catheter 200) from the vascular system of a patient. Snare assembly 10 may be inserted into the vascular system of a patient (e.g., including vessel 202) via an appropriate insertion site (e.g., via the femoral artery) using a vascular sheath (not shown) in a generally conventional manner. Snare assembly 10 may be inserted and delivered to a site of interest as a single step. That is, once the vascular sheath has been inserted into the patient, the assembled catheter 18 and longitudinal shaft 12 (including guide feature 14 and loop 16) may be inserted into the patient together. As such, it may not be necessary to first inserted a guide wire, subsequently deliver a catheter over the guide wire to the site of interest, and then remove the guide wire from the catheter and deliver a snare to the site of interest via the catheter. Accordingly, guide feature 14 may alleviate the need to exchange the snare for a guide wire every time the user wishes to reposition the catheter.

During insertion of snare assembly 10, longitudinal shaft 12 may be positioned relative to catheter 18 such that loop 16 may be stowed within catheter 18, e.g., by being resiliently deformed to a collapsed configuration. Longitudinal shaft 12 may further be positioned relative to catheter 18 such that at least a portion of guide feature 14 may extend beyond the distal end of catheter 18. This relative placement of longitudinal shaft 12 (and guide feature 14) within catheter 18 may allow snare assembly 10 to be advanced through the patient's vascular system as a single unit (i.e., advancing catheter 18 and longitudinal shaft 12 through the patient's vascular system together).

With particular reference to FIGS. 10 and 11, snare assembly 10 may be navigated through branched anatomic lumens by rotationally steering guide feature 14 (alone or together with catheter 18). For example, upon reaching branch 204, snare assembly 10 may be steered to travel through vessel 206 by rotating longitudinal shaft 12 (and thereby also rotating guide feature 14) to orient guide feature 14 to travel from vessel 202 to vessel 206 (e.g., by oriented curved distal end 20 toward vessel 206). Longitudinal shaft 12 (and therein also guide feature 14) may be rotated within catheter 18 (i.e., independently of catheter 18). Additionally/alternatively catheter 18 may be rotated along with longitudinal shaft 12. Navigation of snare assembly through the patient's vascular system may be aided by imaging techniques such as fluoroscopy. Utilizing such imaging techniques, the one or more various radiopaque markers associated with snare assembly 10 may be visible, aiding placement of snare assembly 10 within the patient's anatomy.

Referring to FIG. 12, once snare assembly has been delivered to the site of interest, loop 16 may be deployed from catheter 18 to capture the body to be extracted (i.e., sheared off catheter 200). Loop 16 may be deployed from catheter 18 by moving longitudinal shaft 12 distally relative to catheter 18. That is, longitudinal shaft 12 may be moved distally within vessel 206 while catheter 18 may be maintained in a stationary position. Additionally/alternatively, loop 16 may be deployed from catheter 18 by maintaining longitudinal shaft 12 in a stationary position within vessel 206, and catheter 18 may be retracted proximally relative to longitudinal shaft 12. Further, loop 16 may be deployed by advancing longitudinal shaft 12 within vessel 206 and also retracting catheter 18 within vessel 206.

As discussed above, loop 16 may include a resiliently flexible material (e.g., elastic shape memory alloy, such as Nitinol). Loop 16 may be stowed within catheter 18 by deforming loop 16 (e.g., thereby flattening loop 16 to a width capable of residing within catheter 18). Loop 16 may be resiliently biased to expand to an open configuration when loop 16 is deployed from catheter 18. Accordingly, when loop 16 is deployed from catheter 18, loop 16 may at least partially resiliently recover, thereby at least partially opening up within vessel 206. The at least partially opened loop 16 may be positioned (e.g., by advancing, rotating, etc., longitudinal shaft 12) such that loop 16 may at least partially ensnare or capture the body to be removed (e.g., by at least partially encircling sheared off catheter 200 in the illustrated example). Once loop 16 has been positioned to at least partially encircle sheared off catheter 200, loop 16 may be at least partially closed to secure sheared off catheter 200 relative to snare assembly 10. For example, catheter 18 may be distally advanced over longitudinal shaft 12 such that at least a portion of loop 16 may be stowed within catheter 18. Stowing at least a portion of loop 16 within catheter 18 may at least partially close loop 16 (e.g., by resiliently collapsing loop 16 to fit within catheter 18). At least partially closing loop 16 may cause loop 16 to cinch around sheared off catheter 200, thereby retaining sheared off catheter 200 relative to snare assembly 10. With sheared off catheter 200 retained relative to snare assembly 10, snare assembly 10 and sheared off catheter 200 may be removed from the patient by retracting snare assembly 10, and removing snare assembly 10 from the patient via the vascular sheath.

Referring to FIGS. 13-18, there is shown a procedure for extracting a body (e.g., blood clot 250 in the illustrated example) from an anatomic lumen (e.g., blood vessel 252 in the illustrated example) using snare assembly 10g including a basket-type ensnarement feature (e.g., basket feature 150). In a similar manner as described above, snare assembly 10g may be introduced into a patient's vascular system using a vascular sheath. Snare assembly 10g, including catheter 18, longitudinal shaft 12, guide feature 14, and basket feature 150 may be guided through the patient's vascular system to a site of interest (e.g., the location of blood clot 250 within blood vessel 252). Snare assembly 10g may be guided through the patient's vascular system with basket feature 150 in a generally stowed condition. That is, longitudinal shaft 12, having basket feature 150 associated therewith, may be at least partially retracted relative to catheter 18 such that at least a portion of basket feature 150 is disposed within catheter 18. Further, longitudinal shaft 12 may be positioned relative to catheter 18 such that at least a portion of guide feature 14 (e.g., at least curved distal end 20) may be disposed beyond the distal end of catheter 18. Accordingly, guide feature 14, at least partially extending beyond the distal end of catheter 18 may be used to steer snare assembly 10g through the patient's vascular system without the need to first insert a guide wire.

Figure 13:
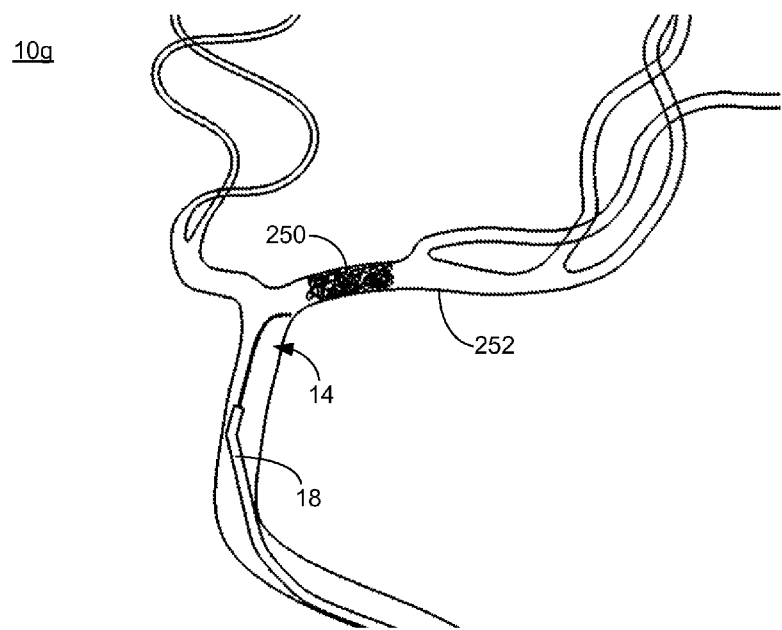
FIGS. 13-18 depict the snare assembly of FIG. 9 utilized for extracting a blood clot from a vascular lumen.
Figure 14:
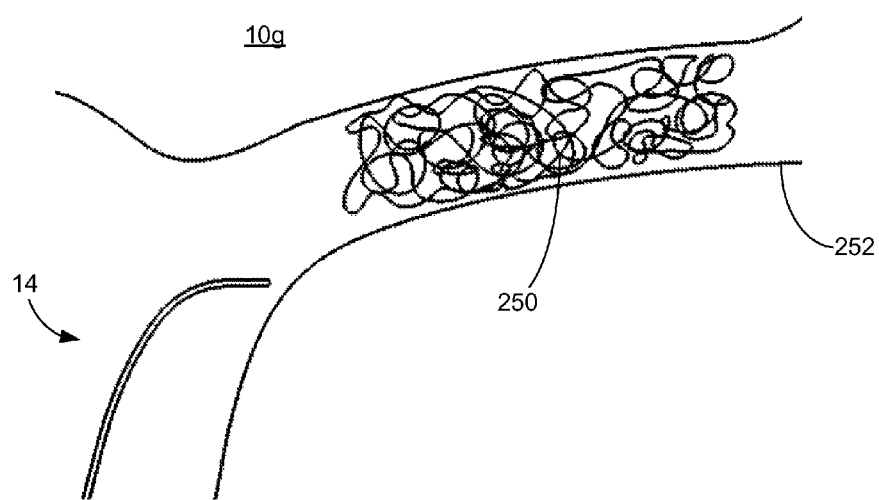

With particular reference to FIGS. 13 and 14, snare assembly 10g may be guided through the patient's vascular system (in the instant example) by rotating at least longitudinal shaft 12 (and therein also rotating guide feature 14) to control the movement of snare assembly 10g through the desired branches and vessels of the patient's vascular system, generally as discussed above. Additionally, and as also generally discussed above, snare assembly 10g may include various radiopaque markers associated with one or more of catheter 18, longitudinal shaft 12, guide feature 14, and basket feature 150. The radiopaque markers may be used in conjunction with an imaging system to aid the user in navigating snare assembly 10g to the desired anatomic location (e.g., the location of blood clot 250 within vessel 252.

Figure 15:
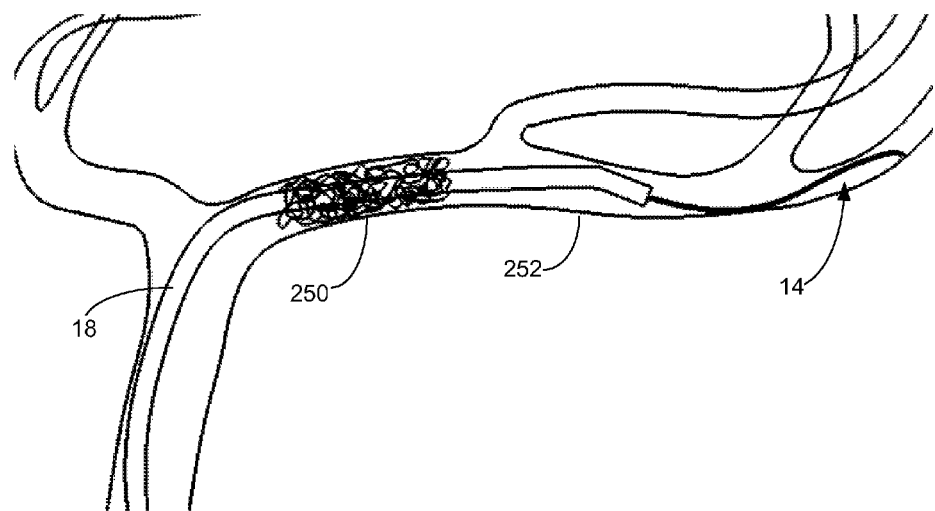

Referring also to FIG. 15, at least a portion of snare assembly 10g may be inserted through vessel 252 at least partially past blood clot 250. Accordingly to various implementations, at least a portion of guide feature 14 and at least a portion of the distal end of catheter 18 may be inserted through vessel 252 past blood clot 250. In various other embodiments longitudinal shaft 12 may be advanced distally relative to catheter 18. In such an embodiment the distal end of catheter 18 may remain proximal blood clot 250, while at least a portion of one or more of longitudinal shaft 12, guide feature 14 and basket feature 150 may be advanced through vessel 252 beyond blood clot 250.

Figure 16:
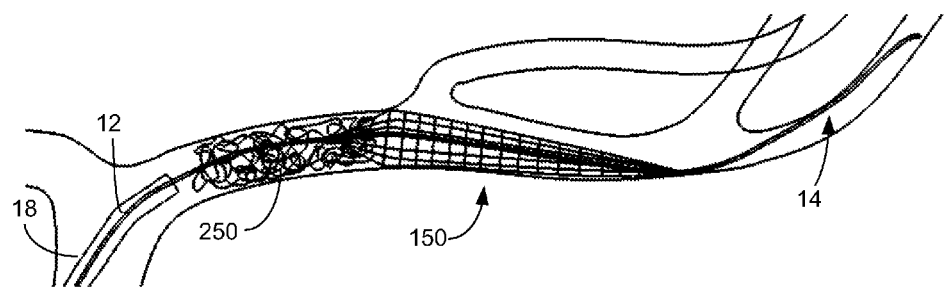
Figure 17:
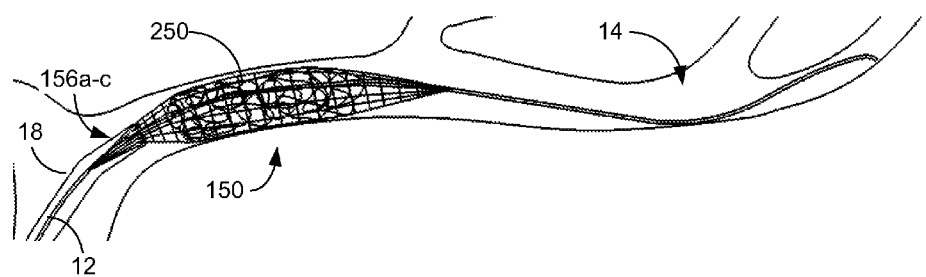
Figure 18:
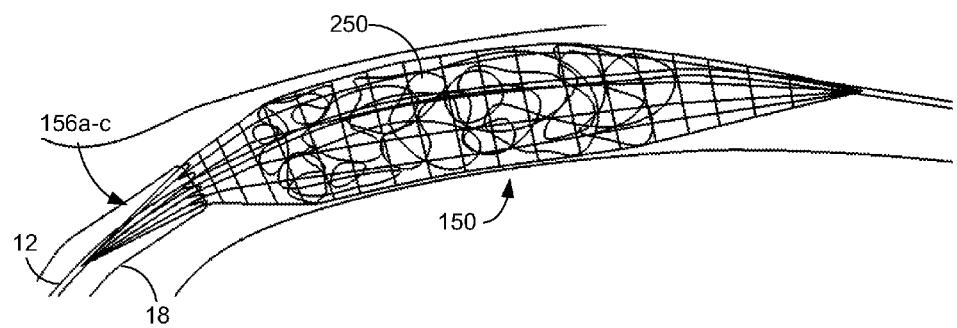
Figure 19:
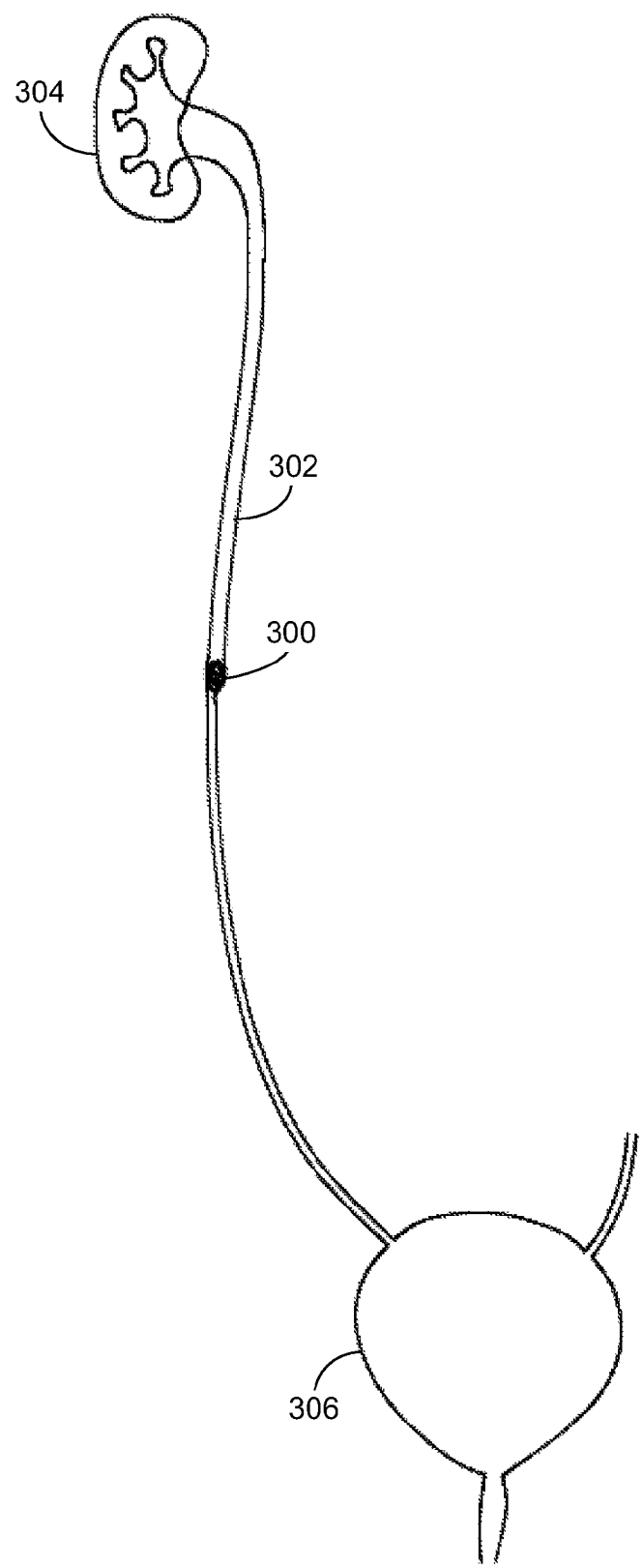
FIGS. 19-26 depict an embodiment of a snare assembly utilized for extracting a stone from a ureter.
Figure 20:
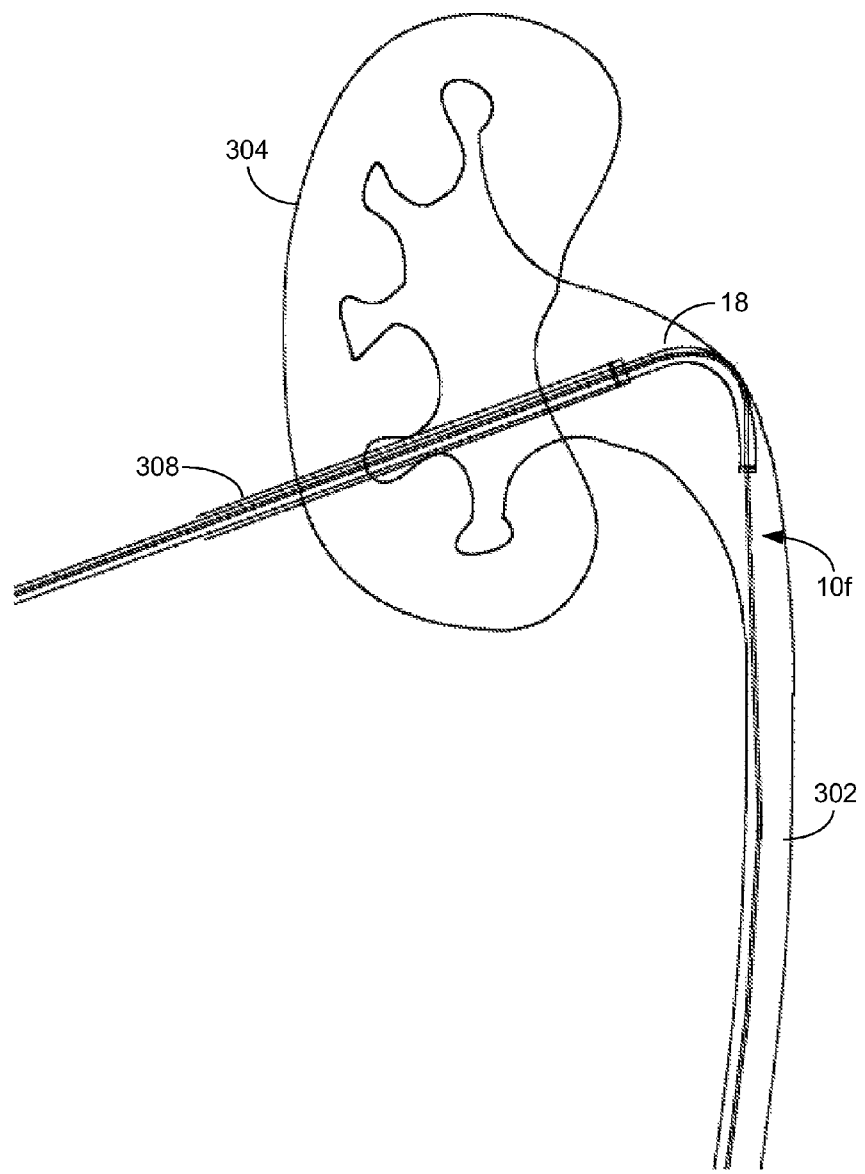

As shown in FIG. 16, basket feature 150 may be deployed distally of blood clot 250, relative to snare assembly 10g. For example, in the illustrated example, snare assembly 10g may be inserted through vessel 252 until at least a portion of longitudinal shaft 12, guide feature 14, the distal end of catheter 18 and basket feature 150 (disposed at least partially within catheter 18) are disposed distally of blood clot 250 within vessel 252. Catheter 18 may then be retracted within vessel 252 to a location proximal blood clot 250. Longitudinal shaft 12, including basket feature 150 associated therewith, may be maintained distal of blood clot 250 while catheter 18 is retracted.

Basket feature 150 may be opened as a result of blood flow through vessel 252 in a direction generally distally of snare assembly 10g. In such a circumstance the blood flow distally relative to basket feature 150 may cause basket feature 150 to open (e.g., to generally conform to the inner walls of vessel 252. Additionally/alternatively, snare assembly 10g may be inserted such that basket feature 150 may be deployed distally of blood clot 250 within vessel 252. Longitudinal shaft 12 may then be retracted within vessel 252 toward blood clot 250. The relative proximal motion of basket feature 150 within vessel 252 may cause basket feature 150 to open. In either case, once basket feature 150 has opened, proximal opening 154 of basket feature 150 may be exposed to blood clot 250. Basket feature 150 may be retracted towards blood clot 250, therein allowing blood clot 250 to enter basket feature 150 through proximal opening 154.

Once blot clot 250 has entered basket feature 150, snare assembly 10g may be retracted from the patient, thereby extracting blood clot 250 from the patient's vascular system. In one embodiment, retracting snare assembly 10g from the patient may include moving longitudinal shaft 12 (and therein also moving basket feature 150) proximally relative to catheter 18. Moving basket feature 150 proximally relative to catheter 18 may cause the distal end of catheter 18 to engage arms 156a, 156b, 156c of basket feature 150. The engagement of arms 156a, 156b, 156c by the distal end of catheter 18 may cause basket feature 150 to at least partially close. For example, engagement of arms 156a, 156b, 156c by the distal end of catheter 18 may cause proximal opening 154 of basket feature 150 to at least partially close. As such, blood clot 250 may be less susceptible to becoming dislodged from basket feature 150.

As discussed above, a snare assembly may be utilized for performing various procedures (e.g., extracting a body) from a variety of anatomic lumens. With reference to FIGS. 19-26, an illustrative implementation is shown for extracting a stone (e.g., urinary stone 300) from a ureter (e.g., ureter 302), between kidney 304 and bladder 306. According to the illustrative example, and referring also to FIG. 20, a first snare assembly (e.g., snare assembly 10f, described herein above) may be introduced into ureter 302 via kidney 203. Snare assembly 10f may be introduced into kidney 304 using introducer sheath 308. As is commonly known, an introducer sheath (e.g., introducer sheath 308) may be used, e.g., for percutaneous insertion of a catheter (e.g., catheter 18) to an internal situs (e.g., kidney 304 in the instant example). For example, introducer sheath 308 may allow snare assembly 10f to be inserted into the inferior posterior calyx of kidney 304. From kidney 304, snare assembly 10f (alone and/or in combination with catheter 18 associated with snare assembly 10f) may be guided into ureter 302 (e.g., by steering and advancing snare assembly 10f using guide feature 14 in a manner similar to that described above in the previous examples).

Figure 21:
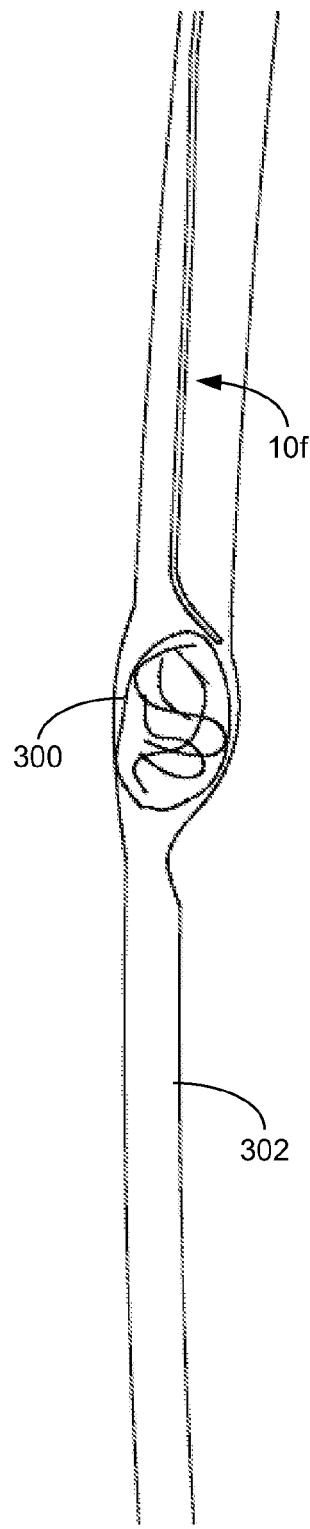
Figure 22:
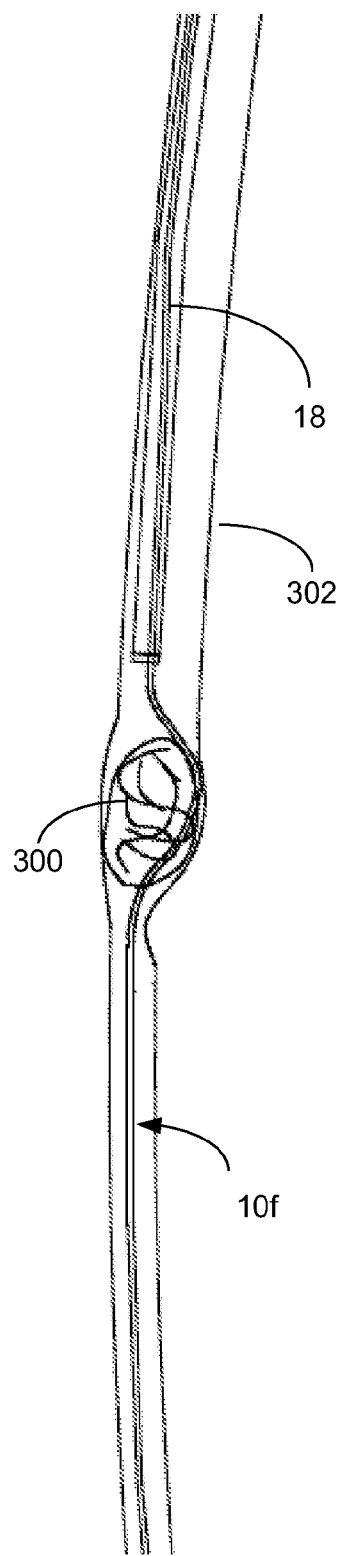
Figure 23:
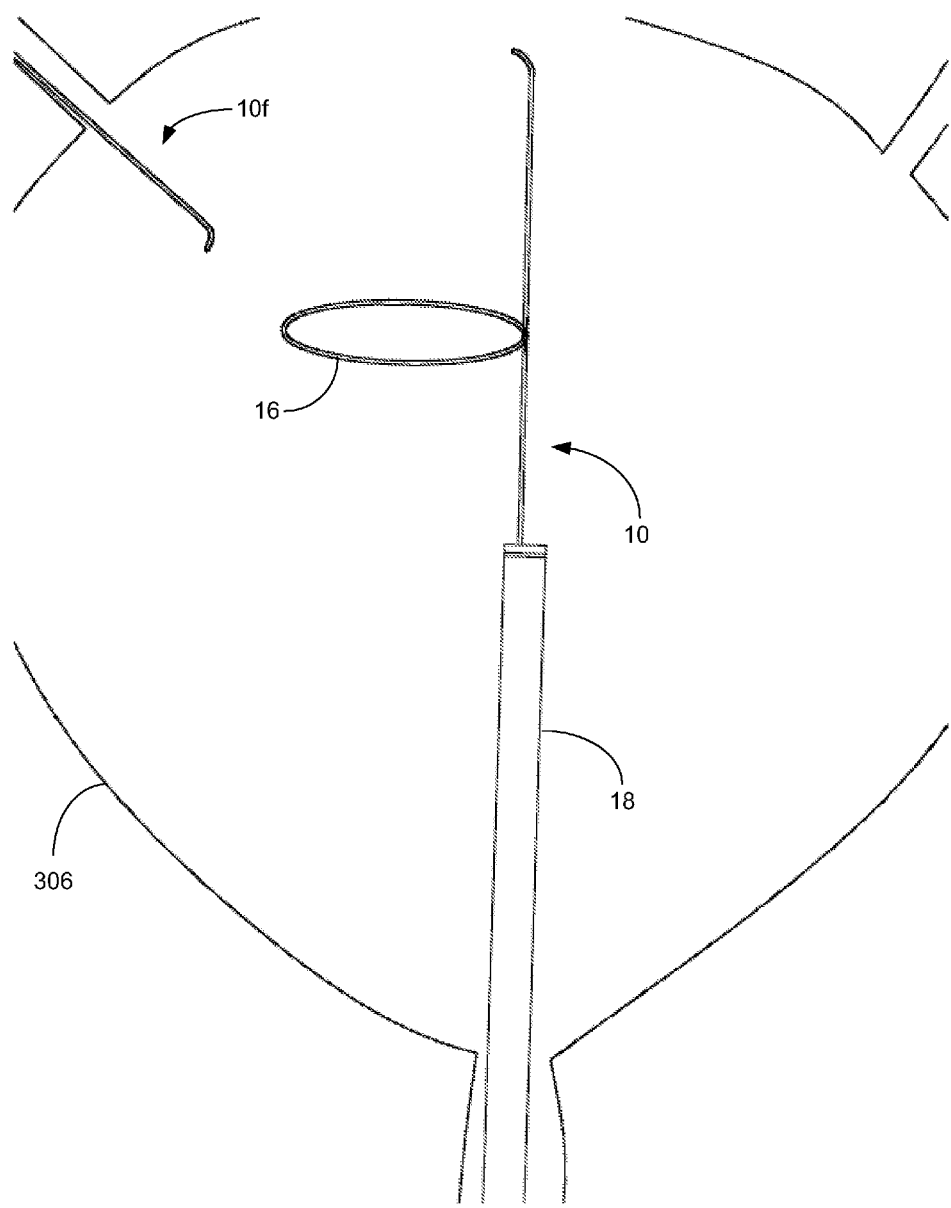

Continuing with the above-stated example, and referring also to FIGS. 21 and 22, in a particular embodiment snare assembly 10f may be advanced through ureter 302 and past stone 300. As discussed above, snare assembly 10f (as well as catheter 18 associated with snare assembly 10f and introducer sheath 308) may include various radiopaque features that may allow the position of snare assembly 10f (as well as catheter 18 associated with snare assembly 10f and introducer sheath 308) to be ascertained using various imaging techniques (e.g., fluoroscopy, etc.). Upon reaching stone 300 located in ureter 302, snare assembly 10f (e.g., including guide feature 14) may be negotiated around stone 300. For example, as described above, guide feature 14 may be steered around stone 300 by rotating longitudinal shaft 12, thereby causing rotation of guide feature 14. Accordingly, guide feature 14 may be positioned to deflect around stone 300. In this manner, snare assembly 10f may be negotiated around, and advanced past stone 300, as shown in FIG. 22.

Figure 24:
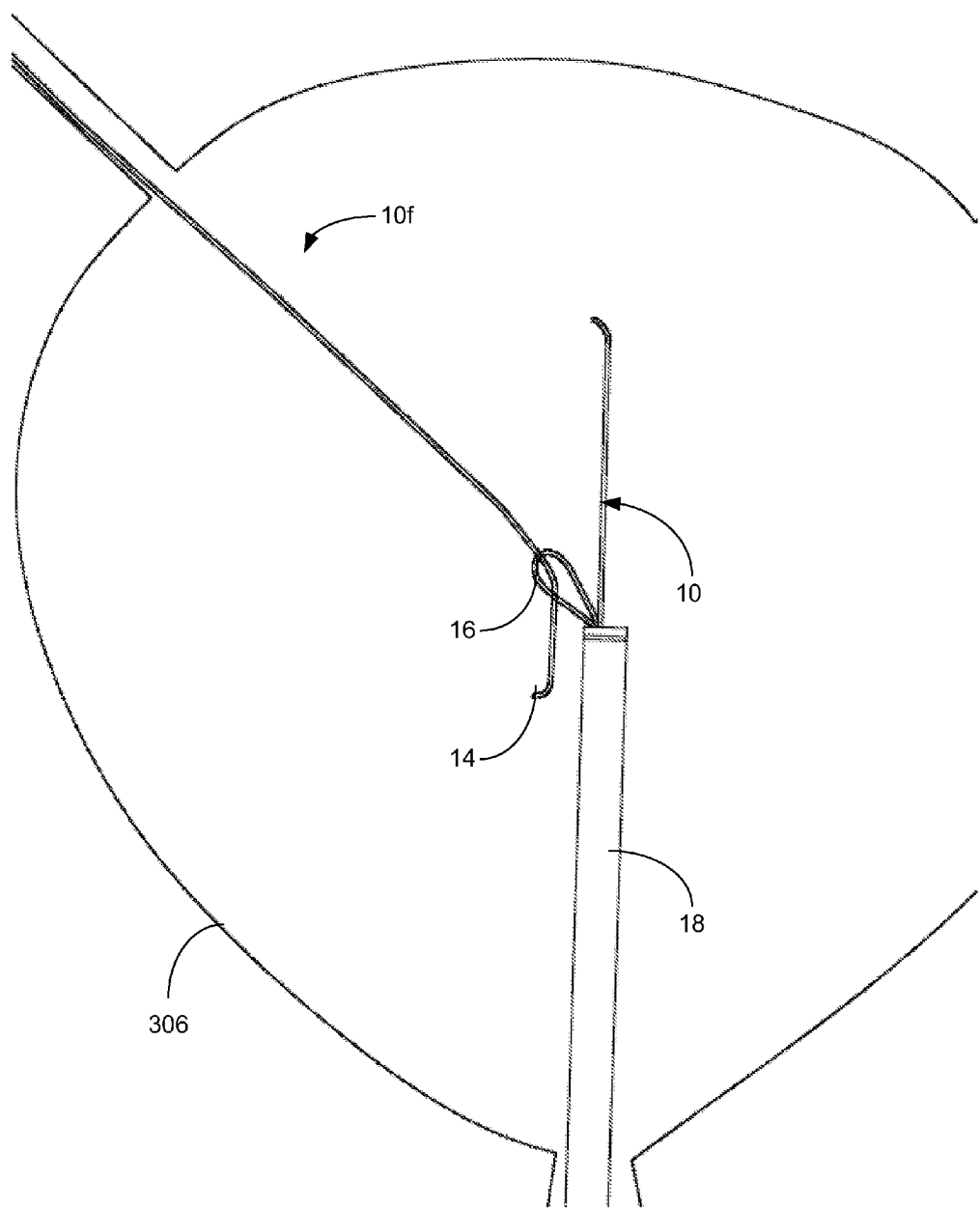

In a particular embodiment, snare assembly 10f may be advanced through ureter 302 and into the urinary bladder (e.g., bladder 306). In a generally corresponding manner, snare assembly 10 may be inserted into bladder 306. For example, snare assembly 10 may be inserted into bladder 306 via the urethra 310. In various other embodiments, snare assembly 10 may be inserted into bladder 306 via percutaneous insertion (e.g., utilizing an introducer sheath). Referring also to FIG. 24, snare assembly 10f and snare assembly 10 may be brought to intersection (e.g., by steering and advancing one or more of snare assembly 10f and snare assembly 10 within bladder 306). At least a portion of snare assembly 10f (e.g., guide feature 14 of snare assembly 10f) may be captured by snare assembly 10. For example, and as described above, guide feature 14 of snare assembly 10f may be inserted into loop 16 of snare assembly 10. With at least a portion of guide feature 14 of snare assembly 10f inserted into loop 16 (e.g., which may require various advancement and rotation of snare assembly 10 in a similar manner as previously described), snare assembly 10 may be retracted relative to catheter 18 associated with snare assembly 10, and/or catheter 18 associated with snare assembly 10 may be advanced relative to snare assembly 10. Once at least a portion of snare assembly 10f has been captured by snare assembly 10, both a proximal end of snare assembly 10f (e.g., an end of snare assembly 10f extending outside of the patient's body via introducer sheath 308) and a distal end of snare assembly 10f (e.g., which may be captured by snare assembly 10) may be controlled. For example, the proximal and distal ends of snare assembly 10f may be controlled for advancement (e.g., by advancing snare assembly 10f, by retracting snare assembly 10, or both in concert) and retraction (e.g., by retracting snare assembly 10f, advancing snare assembly 10, or both in concert).

Figure 25:
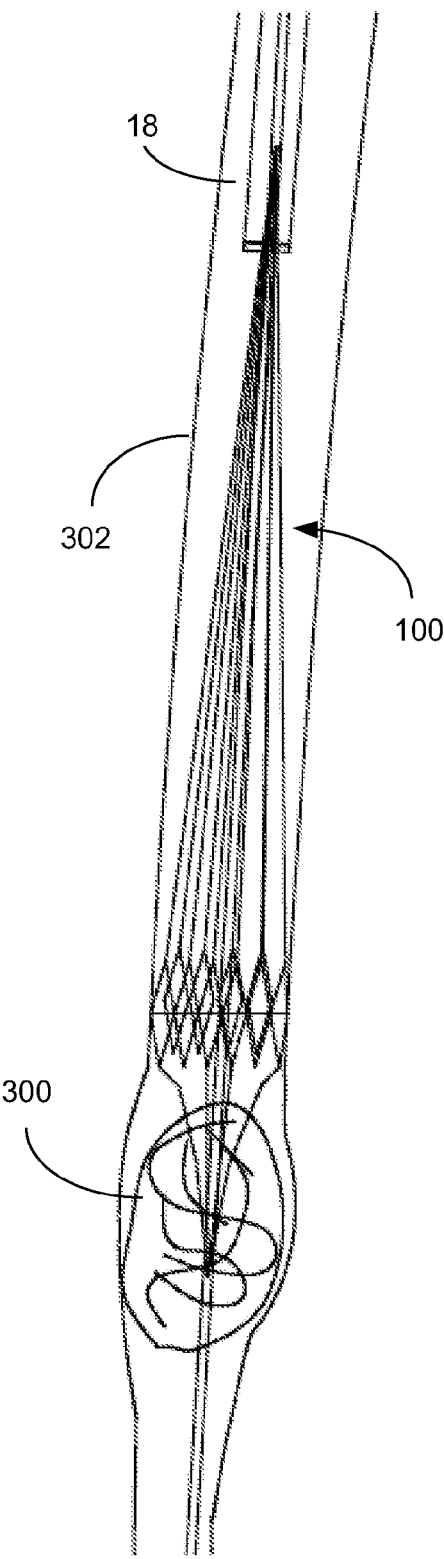
Figure 26:
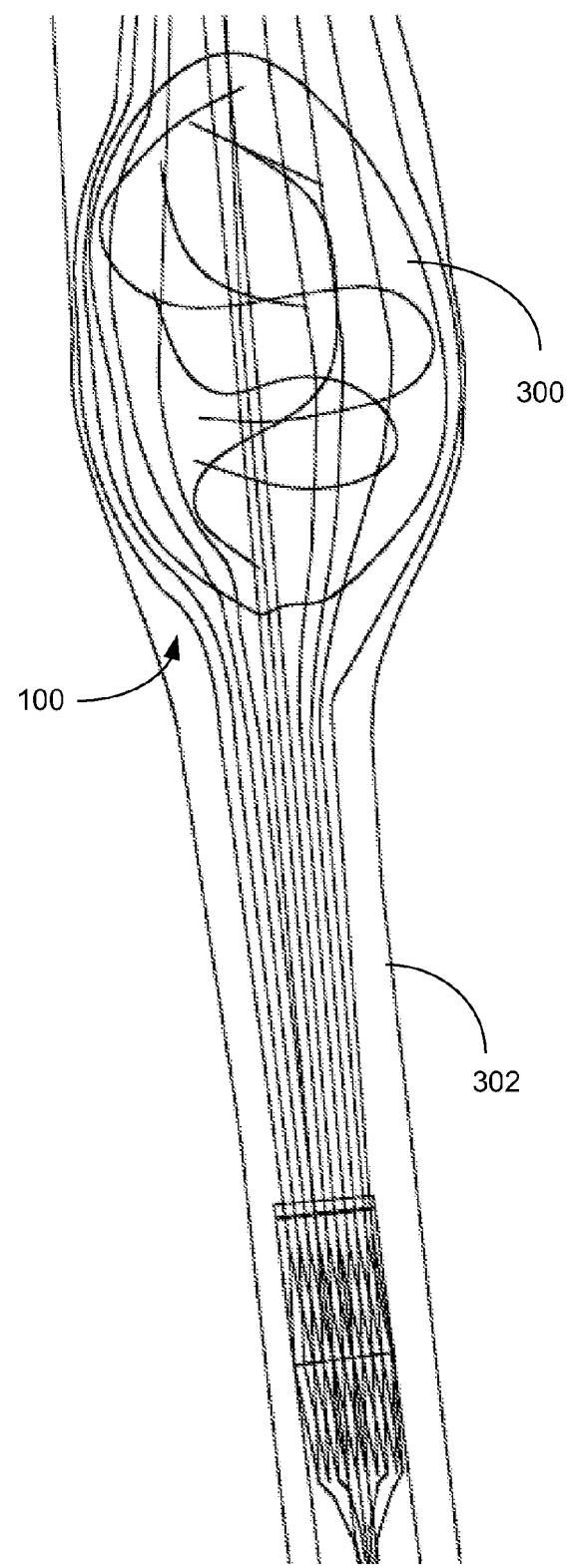

Referring also to FIGS. 25 and 26, snare assembly 10f may be retracted to a position adjacent to stone 300. Once positioned in a desired location relative to stone 300, basket feature 100 of snare assembly 10f may be deployed (e.g., by advancing snare assembly 10f relative to catheter 18 associated with snare assembly 10f). Basket feature 100 may be moved to engage stone 300 (e.g., by controlling one or more of the proximal end of snare assembly 10f and/or the distal end of snare assembly 10f via snare assembly 10, as described above). Basket feature 100 of snare assembly 10f may be controlled to capture stone 300 (in a manner similar to that discussed in previous examples), and basket feature 100 may be at least partially closed around stone 300 (e.g., by retracting snare assembly 10 relative to catheter 18, advancing catheter 18 relative to snare assembly 10f, or both). Once basket feature 100 is at least partially closed around stone 300, stone 300 may be removed from the body, either through kidney 304 (e.g., through introducer sheath 308), or through bladder 306 (e.g., through urethra 310). Additionally, should stone 300 fragment, basket feature 100 may contain at least a portion of the fragments and allow such fragments to be extracted along with stone 300.

As described in the several preceding examples, various snare assemblies may be utilized (alone and/or in combination with other snare assemblies, and/or other surgical equipment) to extract various bodies from various anatomic lumens or cavities. Accordingly, the present disclosure should not be construed as being limited to the described illustrative examples. Various additional/alternative implementations may equally be utilized.

A number of implementations have been described. Nevertheless, it will be understood that various modifications may be made. Accordingly, other implementations are within the scope of the following claims.

What is claimed is:
1. An apparatus comprising:
a plurality of strands twisted together to define a longitudinal shaft;
a guide feature integrally associated with the longitudinal shaft and disposed at a distal end of the longitudinal shaft, the guide feature comprising a strand of the longitudinal shaft, wherein the guide feature is curved such that a distal tip of the guide feature is offset from a longitudinal axis of the longitudinal shaft; and
an ensnarement feature integrally associated with the longitudinal shaft, the ensnarement feature comprising a strand of the longitudinal shaft separated from the plurality of strands to form a loop of the ensnarement feature which rejoins with the plurality of strands of the longitudinal shaft to form the guide feature, wherein the ensnarement feature is disposed proximal the guide feature;
wherein the distal tip of the guide feature and the ensnarement feature are orientated such that the distal tip of the guide feature and the ensnarement feature are disposed on the same side of a plane that includes the longitudinal axis of the longitudinal shaft.

2. The apparatus according to claim 1, wherein the plurality of strands are formed from a resiliently flexible material.

3. The apparatus according to claim 1, wherein the strands of the longitudinal shaft comprise metallic wires.

4. The apparatus according to claim 1, wherein the strands of the longitudinal shaft comprise carbon fibers.

5. The apparatus according to claim 1, wherein the longitudinal shaft includes a hydrophilic surface.

6. The apparatus according to claim 1, wherein the guide feature is curved such that a curved portion of the guide feature is substantially coplanar with a longitudinal portion of the guide feature.

7. The apparatus according to claim 1, wherein the ensnarement feature includes at least one loop.

8. The apparatus according to claim 7, wherein the at least one loop is oriented at an angle relative to an axis of the longitudinal shaft.

9. The apparatus according to claim 1, further including a catheter including a longitudinal lumen configured to slidingly receive at least a portion of the longitudinal shaft.

10. The apparatus according to claim 1, further including at least one radiopaque marker.

11. An apparatus comprising:
a catheter; and
a snare configured to be at least partially slidably disposed within the catheter, the snare including; a plurality of filaments twisted together to define a longitudinal shaft, a guide feature comprising a filament of the longitudinal shaft positioned at a distal end of the longitudinal shaft, the guide feature providing a curved distal end of the longitudinal shaft and a distal tip, wherein the distal end of the guide feature is offset from a longitudinal axis of the longitudinal shaft and a loop comprising a filament separated from the plurality of filaments to form the loop where the filament rejoins the plurality of filaments of the longitudinal shaft to form the guide feature, wherein the loop is disposed proximal the guide feature, wherein the guide feature and the loop are orientated such that the guide feature and the loop are disposed on the same side of a plane that includes the longitudinal axis of the longitudinal shaft.

12. The apparatus according to claim 11, wherein the one or more filaments are disposed within a hydrophilic sheath.

* * * * *